US009669088B2

(12) United States Patent
Podda et al.

(10) Patent No.: US 9,669,088 B2
(45) Date of Patent: Jun. 6, 2017

(54) VACCINATION WITH MULTIPLE CLADES OF H5 INFLUENZA A VIRUS

(75) Inventors: Audino Podda, Sovicille (IT); Rino Rappuoli, Castelnuovo Berardenga (IT)

(73) Assignee: Seqirus UK Limited, Berkshire (GB)

( * ) Notice: Subject to any disclaimer, the term of this patent is extended or adjusted under 35 U.S.C. 154(b) by 887 days.

(21) Appl. No.: 12/744,920

(22) PCT Filed: Nov. 25, 2008

(86) PCT No.: PCT/IB2008/003580

§ 371 (c)(1), (2), (4) Date: May 26, 2010

(87) PCT Pub. No.: WO2009/068992

PCT Pub. Date: Jun. 4, 2009

(65) Prior Publication Data

US 2011/0189230 A1 Aug. 4, 2011

Related U.S. Application Data

(60) Provisional application No. 61/004,334, filed on Nov. 26, 2007.

(30) Foreign Application Priority Data

Jun. 5, 2008 (GB) .................................. 0810305.3

(51) Int. Cl.

| | |
|---|---|
| ***A61K 39/145*** | (2006.01) |
| ***C07K 14/11*** | (2006.01) |
| ***A61K 39/12*** | (2006.01) |
| *A61K 39/00* | (2006.01) |

(52) U.S. Cl.

CPC ............ *A61K 39/145* (2013.01); *A61K 39/12* (2013.01); *A61K 2039/5256* (2013.01); *A61K 2039/5258* (2013.01); *A61K 2039/53* (2013.01); *A61K 2039/545* (2013.01); *A61K 2039/55566* (2013.01); *C12N 2710/10343* (2013.01); *C12N 2760/16134* (2013.01)

(58) Field of Classification Search

None

See application file for complete search history.

(56) References Cited

U.S. PATENT DOCUMENTS

| | | | | |
|---|---|---|---|---|
| 8,080,255 B2 | 12/2011 | Smith et al. | | |
| 2007/0141078 A1* | 6/2007 | D'Hondt et al. | .......... | 424/204.1 |
| 2008/0014217 A1* | 1/2008 | Hanon | ................. | A61K 39/145 424/209.1 |

FOREIGN PATENT DOCUMENTS

| | | |
|---|---|---|
| WO | WO-02/080648 | 10/2002 |
| WO | WO-2006/041978 A2 | 4/2006 |
| WO | WO-2006/050394 | 5/2006 |
| WO | WO-2006/100109 A1 | 9/2006 |
| WO | WO-2006/100110 A1 | 9/2006 |
| WO | WO-2007/052057 | 5/2007 |
| WO | WO-2007/052155 | 5/2007 |
| WO | WO-2007/130330 A2 | 11/2007 |
| WO | WO-2008/009309 A1 | 1/2008 |

OTHER PUBLICATIONS

Stephenson et al. (Vaccine. 2003; 21: 1687-1693).*
Stephenson et al. (The Lancet. Aug. 2004; 499-509).*
Bender et al. (Virology. 1999; 254: 115-123).*
Chen et al. (Nature. Jul. 2005; 436: 191-192).*
Govorkova et al. (Journal of Infectious Diseases. Electronically published Jun. 9, 2006; 194: 159-167).*
Alving (Vaccine. 2002; 20: S56-S64).*
European Search Report mailed Jun. 14, 2013, for European Application No. 12198671, 1 page.
NIH News (2006). "New tool helps identify mysterious viruses that caused New York respiratory illness in 2004," retrieved from the internet on Aug. 9, 2013, at <www.niaid.nih.gov/news/newsreleases/2006/Pages/masstag.aspx>.
Oh et al. (Aug. 2010). "An antibody against a novel and conserved epitope in the hemagglutinin 1 subunit neutralized numerous H5N1 influenza viruses," J Virol 84(16):8275-86.
Poland et al. (Apr. 2007). "Avian and pandemic influenza: an overview," Vaccine 25(16):3057-61.
Bresson et al. (May 20, 2006). "Safety and immunogenicity of an inactivated split-virion influenza A/Vietnam/1194/2004 (H5N1) vaccine: phase I randomised trial," Lancet 367(9523):1657-1664.
Chun-yan et al. (Feb. 2007). "Serum-free culture of vero cells and influenza virus on microcarrier," Chin J Biologicals 20(2):125-128.
Crevar & Ross (2008) "Elicitation of protective immune responses using a bivalent H5N1 VLP vaccine," Virol J 5:131.
Haaheim, L R (2003). "Original antigenic sin. A confounding issue?" Dev. Biologicals 115:49-53.
Hoelscher et al. (Apr. 15, 2008). "A broadly protective vaccine against globally dispersed clade 1 and clade 2 H5N1 influenza viruses," J Infect Dis 197(8):1185-1188.
International Search Report mailed Feb. 26, 2009, for PCT Application No. PCT/IB2008/003580 filed Nov. 25, 2008, 3 pages.
Keitel et al. (Oct. 1, 2007). "Preparing for a possible pandemic: influenza A/H5N1 vaccine development," Curr Opin Pharmacol 7(5):484-490.

(Continued)

*Primary Examiner* — Shanon A Foley

(74) *Attorney, Agent, or Firm* — Finnegan, Henderson, Farabow, Garrett & Dunner, LLP

(57) ABSTRACT

H5N1 influenza viruses isolated from animals and humans since 2003 separate into distinct clades based on hemagglutinin amino acid sequences. According to the invention, multiple clades are used in influenza immunization. Thus there is a prime-boost immunization schedule where a subject receives a priming dose of a first clade of H5 influenza A virus and a boosting dose of a second clade of H5 influenza A virus. There is also an immunogenic composition comprising hemagglutinin antigens from more than one clade of H5 influenza A virus.

24 Claims, 2 Drawing Sheets

(56) References Cited

OTHER PUBLICATIONS

Rao et al. (Jun. 2008). "Multivalent HA DNA vaccination protects against highly pathogenic H5N1 avian influenza infection in chickens and mice," PLoS One 3(6):e2432.
Simmons et al. (May 2007). "Prophylactic and therapeutic efficacy of human monoclonal antibodies against H5N1 influenza," PLoS Med 4(5):e178.
Stephenson et al. (Apr. 2, 2003). "Boosting immunity to influenza H5N1 with MF59-adjuvanted H5N3 A/Duck/Singapore/97 vaccine in a primed human population," Vaccine 21(15):1687-1693.
Stephenson et al. (May 2006). "Phase I Evaluation of Intranasal Trivalent Inactivated Influenza Vaccine with Nontoxigenic *Escherichia coli* Enterotoxin and Novel Biovector as Mucosal Adjuvants, Using Adult Volunteers," J Virol 80(10):4962-4970.
Stephenson et al. (Oct. 9, 2008). "Antigenically distinct MF59-adjuvanted vaccine to boost immunity to H5N1," NEJM 359(15):1631-1633.
Stephenson et al. "Antigenically Distinct MF59-Adjuvanted Vaccine to Boost Immunity to H5N1" The New England Journal of Medicine 359:15 1631-1633 (2008).
Lipsitch et al. "Patterns of antigenic diversity and the mechanisms that maintain them" Journal of The Royal Society 4: 787-802 (2007).
Carrat et al. "Influenza vaccine: The challenge of antigenic drift" Vaccine 25: 6852-6862 (2007).
Smith et al. "Evolution and adaptation of H5N1 influenza virus in avian and human hosts in Indonesia and Vietnam" Virology 350: 258-268 (2006).
Belshe et al. (2011). "Safety and immunogenicity of influenza A H5 subunit vaccines: effect of vaccine schedule and antigenic variant," J Infect Dis, 203(5):666-73.
European Centre for Disease Prevention and Control (ECDC) Technical Report, Expert Advisory Groups on human H5N1 vaccines, Aug. 2007, 36 pages.
Forrest et al. (2009). "Single- and multiple-clade influenza A H5N1 vaccines induce cross protection in ferrets," Vaccine, 27(31):4187-95.
Fragapane et al. (2010). "A heterologous MF59-adjuvanted H5N1 prepandemic influenza booster vaccine induces a robust, cross-reactive immune response in adults and the elderly," Clin Vaccine Immunol, 17(11):1817-9.
Fukuda (2004). "Inactivated Influenza Vaccines" Chapter 17 in "Vaccines," Fourth Edition, Plotkin et al (Eds), Saunders, pp. 339-370.
Galli et al. (2009). "Fast rise of broadly cross-reactive antibodies after boosting long-lived human memory B cells primed by an MF59 adjuvanted prepandemic vaccine," Proc Natl Acad Sci U S A, 106(19):7962-7.
Gillard et al. (2014). "Long-term booster schedules with AS03A-adjuvanted heterologous H5N1 vaccines induces rapid and broad immune responses in Asian adults," BMC Infect Dis, 14:142.
Goji et al. (2008). "Immune responses of healthy subjects to a single dose of intramuscular inactivated influenza A/Vietnam/1203/2004 (H5N1) vaccine after priming with an antigenic variant," J Infect Dis, 198(5):635-41.
Influenza Team (Sep. 20, 2007). "Human influenza A/H5N1 ("pre-pandemic") vaccines: informing policy development in Europe," Eurosurveillance, vol. 12, issue 38, retrieved Jan. 6, 2015 from http://www.eurosurveillance.org/ViewArticle.aspx?ArticleId=3272.
Influenza Virus Vaccine H5N1, Highlights of prescribing information, published Apr. 2007 by Sanofi Pasteur, 16 pages.
Kistner et al. (2007). "Cell culture (Vero) derived whole virus (H5N1) vaccine based on wild-type virus strain induces cross-protective immune responses," Vaccine, 25(32):6028-36.
Kistner et al. (2008). "Induction of cross-clade anti-H5N1 immune responses in mice, guinea pigs and ferrets by Vero cell-derived H5N1 whole virus candidate vaccines," Poster presentations, The third European Influenza Conference, p. 34.
Leroux-Roels et al. (2007). "Antigen sparing and cross-reactive immunity with an adjuvanted rH5N1 prototype pandemic influenza vaccine: a randomised controlled trial," Lancet, 370(9587):580-9.
Li et al. (2007). "Development of vaccines against influenza A virus (H5N1).," Chang Gung Med J, 30(4):294-304.
NIH press release, "Updates on Pandemic Flu Vaccine Trials to be Presented at 44th Annual IDSA Meeting," NIH News, dated Oct. 12, 2006, 3 pages.
Nolan et al. (2006). "Immune responses of healthy subjects to a single dose of intramuscular inactivated influenza A/Vietnam/1203/2004 (H5N1) vaccine after priming with an antigenic variant," Late Breaker Symposium session, Infectious Diseases Society of America, 1 page.
Notice of Opposition by GlaxoSmithKline Biologicals S.A., filed in opposition against EP2211901, dated Jan. 31, 2014, 27 pages.
Preliminary non-binding opinion of the Opposition Division, filed in oppostion filed in opposition against EP2211901, dated Apr. 13, 2015, 11 pages.
Response to Notice of Opposition by patentee, filed in opposition against EP2211901, dated Sep. 23, 2014, 16 pages.
Stephenson (2005). "Are we ready for pandemic influenza H5N1?" Expert Rev Vaccines, 4(2):151-5.
Treanor et al. (2001). "Safety and immunogenicity of a recombinant hemagglutinin vaccine for H5 influenza in humans," Vaccine, 19(13-14):1732-7.
Treanor et al. (2006). "Safety and immunogenicity of an inactivated subvirion influenza A (H5N1) vaccine," N Engl J Med, 354(13):1343-51.
Van der Velden et al. (2012). "Cell culture (Vero cell) derived whole-virus non-adjuvanted H5N1 influenza vaccine induces long-lasting cross-reactive memory immune response: homologous or heterologous booster response following two dose or single dose priming," Vaccine, 30(43):6127-35.
WHO (Oct. 2011). "Updated unified nomenclature system for the highly pathogenic H5N1 avian influenza viruses," Retrieved Jan. 29, 2014 from http://www.who.int/influenza/gisrs_laboratory/h5n1_nomenclature/en/.
WHO/OIE/FAO H5N1 Evolution Working Group. (2008). "Toward a unified nomenclature system for highly pathogenic avian influenza virus (H5N1)," Emerg Infect Dis, 14(7):e1.
Yang et al. (2012). "Multiple-clade H5N1 influenza split vaccine elicits broad cross protection against lethal influenza virus challenge in mice by intranasal vaccination," PLoS One, 7(1):e30252.
Bjarnarson et al. (2005). "The advantage of mucosal immunization for polysaccharide-specific memory responses in early life," European Journal of Immunology 35(4):1037-1045.
Decision revoking the European patent EP2211901, dated Nov. 26, 2015. 29 pages.
Galli et al. (May 2009). "Fast rise of broadly cross-reactive antibodies after boosting long-lived human memory B cells primed by an MF59 adjuvanted prepandemic vaccine," Proc Natl Acad Sci U S A. 106(19):7962-7967.
Galli et al. (Mar. 2009). "Adjuvanted H5N1 vaccine induces early CD4+ T cell response that predicts long-term persistence of protective antibody levels," Proc Natl Acad Sci U S A. 106(10):3877-82.
Mills et al. (2003). "Protective levels of diphtheria-neutralizing antibody induced in healthy volunteers by unilateral priming-boosting intranasal immunization associated with restricted ipsilateral mucosal secretory immunoglobulin A," Infection and Immunity, 71(2):726-732.
Notice of appeal, filed in relation to EP2211901, dated Feb. 3, 2016, 1 page.
Pittman et al. (2002). "Antibody response to a delayed booster dose of anthrax vaccine and botulinum toxoid," Vaccine 20:2107-2115.
Schosser et al. (2007). "Seroprotection after delayed booster vaccination with FSME-Immun Erwachsene®—preliminary results," IX International Jena Symposium on Tick-borne Diseases. 1 Page.
Stephenson et al. (2003). "Boosting immunity to influenza H5N1 with MF59-adjuvanted H5N3 A/Duck/Singapore/97 vaccine in a primed human population," Vaccine, 21(15):1687-1693.

(56) References Cited

OTHER PUBLICATIONS

WHO (2010-2015). Recommended viruses for influenza vaccines for use in the 2010-2011, 2011-2012, 2013-2014, 2014-2014 northern hemisphere influenza season.
Response to oral proceedings' summons by GlaxoSmithKline, filed in opposition against EP2211901, dated Aug. 26, 2015, 10 pages.
Response to oral proceedings' summons by GlaxoSmithKline, filed in opposition against EP2211901, dated Sep. 16, 2015, 3 pages.
Response to oral proceedings' summons by Novartis, filed in opposition against EP2211901, dated Aug. 27, 2015, 5 pages.
Response with regard to oral proceedings by GlaxoSmithKline, filed in opposition against EP2211901, dated Oct. 22, 2015, 2 pages.
La Montagne et al. (1983). "Summary of clinical trials of inactivated influenza vaccine—1978," Rev Infect Dis, 5(4):723-36.

* cited by examiner

VACCINATION WITH MULTIPLE CLADES OF H5 INFLUENZA A VIRUS

CROSS REFERENCE TO RELATED APPLICATIONS

This is a U.S. National Phase Patent Application of PCT/IB2008/003580, filed Nov. 25, 2008, which claims priority to Provisional Patent Application Ser. No. 61/004,334 filed Nov. 26, 2007 and United Kingdom Patent Application Serial No. 0810305.3, filed Jun. 5, 2008, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002113400Seqlist.txt, date recorded: Sep. 24, 2010, size: 28 KB).

TECHNICAL FIELD

This invention is in the field of vaccines for protecting against influenza virus infection, and in particular for protecting against influenza pandemics.

BACKGROUND ART

Influenza virus strains for use in vaccines change from season to season. For several years, vaccines have typically included two influenza A strains (H1N1 and H3N2) and one influenza B strain. To deal with 'antigenic drift', the precise strains used for vaccination change from year to year.

Of more concern than antigenic drift is 'antigenic shift', in which the subtype of prevailing influenza A viruses changes from H1N1 and H3N2. In particular, it is expected that the H5 subtype of influenza A virus may become prevalent in the near future. As the human population is immunologically naïve to the new hemagglutinin subtype then this antigenic shift will cause a pandemic outbreak of influenza infections. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade, or has not previously been seen at all in the human population; (b) it is capable of being transmitted horizontally in the human population; and (c) it is pathogenic to humans.

In preparing for an influenza pandemic caused by a H5 strain, it has been proposed to use a pre-pandemic vaccination strategy [1]. Patients are immunized with a current H5 strain (from birds) in the hope that the resulting immunity will be useful when the pandemic occurs, despite any antigenic drift that may occur in the meantime.

In October 2006, Sanofi Pasteur announced results on its candidate pre-pandemic vaccine, which was tested in adjuvanted and un-adjuvanted forms at various antigen doses. In November 2006 Novartis Vaccines announced that it was filing for European regulatory approval for an adjuvanted pre-pandemic vaccine. In June 2007 GlaxoSmithKline announced its intention to donate 50 million doses of H5N1 adjuvanted pre-pandemic vaccine to the WHO and in February 2008 its PREPANDRIX™ product received a positive opinion from EMEA's Committee for Medicinal Products for Human Use. All three products have been based on the H5N1/A/Vietnam/1194/04 strain.

DISCLOSURE OF THE INVENTION

H5N1 viruses isolated from animals and humans since 2003 separate into multiple distinct clades (genetic groups) of closely-related viruses based on hemagglutinin amino acid sequences. The H5N1/A/Vietnam/1194/04 strain is classified in clade 1.

According to the invention, multiple clades are used in influenza immunization.

In a first aspect of the invention, a prime-boost immunization schedule is used where a subject receives a priming dose of a first clade of H5 influenza A virus and a boosting dose of a second clade of H5 influenza A virus. For instance, a patient may be primed with a clade 1 antigen and boosted with clade 2, or vice versa.

Similarly, a booster immunization may be given to a patient who has already received a H5 vaccine from a first clade (e.g. clade 1) by using a H5 vaccine from a different clade (e.g. clade 2). The patient will usually have received a full primary course (e.g. two doses) of the first clade vaccine.

In a second aspect, an immunogenic composition may comprise hemagglutinin antigens from multiple clades of H5 influenza A virus, permitting simultaneous immunization against multiple H5 clades.

Thus the invention provides a method for immunizing a patient against influenza virus, comprising steps of (i) administering to a subject an immunogenic composition comprising hemagglutinin antigen from a first clade of H5 influenza A virus, and then (ii) administering to the subject an immunogenic composition comprising hemagglutinin antigen from a second clade of H5 influenza A virus, wherein the first and second clades are different from each other.

The invention also provides a method for immunizing a patient against influenza virus, comprising a step of administering to a subject an immunogenic composition comprising hemagglutinin antigen from a second clade of H5 influenza A virus, wherein the patient has previously received an immunogenic composition comprising hemagglutinin antigen from a first clade of H5 influenza A virus, wherein the first and second clades are different from each other.

The invention also provides an immunogenic composition comprising hemagglutinin antigens from more than one clade of H5 influenza A virus (e.g. 2, 3, 4, 5 or 6 different clades).

The invention also provides an immunogenic composition comprising hemagglutinin antigens from at least two strains (e.g. 2, 3, 4, 5 or 6 different strains) of H5 influenza A virus, wherein a first H5 strain and a second H5 strain are in different clades.

H5 Clades

The hemagglutinin antigens of the viruses used with the invention fall into the H5 subtype, but within the H5 subtype they fall into different clades.

The haemagglutinin (HA) sequences of the majority of H5N1 viruses circulating in avian species since 2003 separate into distinct phylogenetic clades. Clade 1 viruses circulating in Cambodia, Thailand and VietNam were responsible for human infections in those countries during 2004 and 2005, and in Thailand during 2006. Clade 2 viruses have circulated in birds in China and Indonesia since 2003; they spread westwards during 2005 and 2006 to the Middle East, Europe and Africa. Since late 2005, clade 2 viruses have been principally responsible for human infections. Multiple subclades of clade 2 have been distinguished; three of these—subclades 1, 2 and 3 (FIG. 1)—differ in geographical distribution and have so far been largely responsible for human cases.

Between August 2006 and March 2007, the majority of HA sequences of H5N1 viruses that have continued to circulate or have re-emerged in avian species and have been associated with sporadic human infections in Africa, Asia and Europe, fell into the previously designated phylogenetic clades and subclades. Clade 1 viruses were responsible for outbreaks in birds in Thailand and VietNam and for human infections in Thailand. Clade 2.1 viruses continue to circulate in poultry and cause human infections in Indonesia. Clade 2.2 viruses have caused outbreaks in birds in some countries in Africa, Asia and Europe, and have been associated with human infections in Egypt, Iraq and Nigeria. Clade 2.3 viruses have been isolated sporadically in Asia and have been responsible for human infections in China and the Lao People's Democratic Republic.

In addition, a few viruses that fall outside of these classifications were isolated from domestic poultry during localized outbreaks in Asia. These fall into emerging clades, represented by A/goose/Guiyang/337/2006 (clade 4) and A/chicken/Shanxi/2/2006 (clade 7). In total, 10 clades have currently been defined (FIG. 2), numbered 0 to 9.

For reference herein, prototypic strains for each clade are as follows, together with the coding sequence of their hemagglutinin genes:

| Clade | Strain | SEQ ID NO |
|---|---|---|
| 1 | A/HongKong/213/03 | 1 |
| 2 | A/Indonesia/5/05 | 2 |
| 3 | A/Chicken/Hong Kong/SF219/01 | 3 |
| 4 | A/chicken/Guiyang/441/2006 | 4 |
| 5 | A/duck/Guangxi/1681/2004 | 5 |
| 6 | A/tree sparrow/Henan/4/2004 | 6 |
| 7 | A/chicken/Shanxi/2/2006 | 7 |
| 8 | A/Chicken/Henan/12/2004 | 8 |
| 9 | A/duck/Guangxi/2775/2005 | 9 |
| 0 | A/Hong Kong/156/97 | 10 |

A clade 1 H5 virus may be defined herein in phylogenetic terms as an influenza A virus having a hemagglutinin coding sequence that is more closely related to the coding sequence from the A/HongKong/213/03 strain (SEQ ID NO: 1) than to any the coding sequence from any of clades 0 and 2 to 9 (SEQ ID NOs: 2 to 10), when assessed using the DNADIST algorithm as implemented in the Phylip package [2] (e.g. using Kimura 2-parameter distances and a square matrix). Similarly, a clade 2 virus has a hemagglutinin coding sequence that is more closely related to the coding sequence from the A/Indonesia/5/05 strain (SEQ ID NO: 2) than to any the coding sequence from any of clades 0, 1 and 3 to 9 (SEQ ID NOs: 1 and 3 to 10). The other clades are phlyogenetically defined similarly—with a hemagglutinin coding sequence that is more closely related to the relevant coding sequence from SEQ ID NOs: 1 to 10 than to the other sequences in SEQ ID NOs: 1 to 10.

A clade 1 virus may be defined herein in nucleic acid sequence terms as an influenza A virus having a hemagglutinin coding sequence with greater sequence identity to the A/HongKong/213/03 strain (SEQ ID NO: 1) than to any of SEQ ID NOs: 2 to 10. The other clades are defined similarly—with a hemagglutinin coding sequence that is more closely related to the relevant coding sequence from SEQ ID NOs: 1 to 10 than to the other sequences in SEQ ID NOs: 1 to 10.

A H5 virus may be defined herein as being in a particular clade in amino acid sequence terms by reference to characteristic HA mutations [3]. For instance, a clade 3 virus may have one or more of the following amino acid residues, which are distinct from clades 1 and 2: Asn-45; Ser-84; Asn-94; Asn-124; Leu-138; Ser-144; Glu-212; Ser-223; and/or Arg-325. A clade 2 virus may have Asp-124, which is not seen in clades 1 and 3. A clade 1 virus may have one or more of the following amino acid residues, which are distinct from clades 2 and 3: Ser-124; Leu-129.

Within clade 2, at least three subclades have been recognized: 2.1, 2.2 and 2.3 (FIG. 1). A clade 2.1 H5 virus may be defined herein in phylogenetic terms as having a hemagglutinin coding sequence that is more closely related to the A/Indonesia/5/05 strain (SEQ ID NO: 2) than to either the A/Anhui/1/2005 strain (SEQ ID NO: 11) or the A/turkey/Turkey/1/05 (SEQ ID NO: 12). Similarly, a clade 2.2 H5 virus may be defined herein in phylogenetic terms as having a hemagglutinin coding sequence that is more closely related to the A/turkey/Turkey/1/05 strain (SEQ ID NO: 12) than to either the A/Anhui/1/2005 (SEQ ID NO: 11) or the A/Indonesia/5/05 strain (SEQ ID NO: 2). Finally, a clade 2.3 H5 virus may be defined herein in phylogenetic terms as having a hemagglutinin coding sequence that is more closely related to the A/Anhui/1/05 strain (SEQ ID NO: 11) than to either the A/turkey/Turkey/1/05 (SEQ ID NO: 12) or the A/Indonesia/5/05 strain (SEQ ID NO: 2).

In some embodiments a strain in subclade 2.2 may have HA including one or more of the following sequences: Ile-223; Ile-230; Ser-294; Ile-517; ΔSer-133; a cleavage site having sequence REGRRRKR (SEQ ID NO: 13); a cleavage site having sequence GERRRRKR (SEQ ID NO: 16). The HA gene may include one or more of nucleotides: A-41; A-142; A-209; A-295; G-433; A-467; A-496; C-610; A-627; A-643; C-658; T-661; T-689; T-727; A-754; G-880; C-937; G-1006; T-1012; A-1019; T-1177; A-1235; T-1402; C-1415; T-1480; C-1510; T-1614; C-1615; A-1672; G-1708 (any of which may or may not change the encoded amino acid for the relevant codon). The NA gene may include nucleotide A-743, which will not change the encoded amino acid for the relevant codon.

In some embodiments of the invention, the priming antigen and/or the boosting antigen is not from clade 0 e.g. is not from strain A/Hong Kong/156/97. For instance, if the second antigen is from clade 1 (e.g. A/Vietnam/1203/2004) then the first antigen is preferably not from clade 0 (e.g. A/Hong Kong/156/97)

Clade Combinations

The invention uses antigens derived from more than one H5 clade for immunization.

For instance, a patient may be primed with antigen from a H5 virus in a first clade, but then boosted with antigen from a H5 virus in a second clade. Useful clade combinations in this prime/boost strategy include but are not limited to the following:

| | | | | | | | | | | | | |
|---|---|---|---|---|---|---|---|---|---|---|---|---|
| Prime | 1 | 2 | 1 | 1 | 2 | 2 | 1 | 1 | 1 | 2.1 | 2.2 | 2.3 |
| Boost | 2 | 1 | 4 | 7 | 4 | 7 | 2.1 | 2.2 | 2.3 | 1 | 1 | 1 |

The invention also provides a booster immunization for a patient previously primed with antigen from a H5 virus in a first clade, wherein the booster is from a second (different) clade. The above combinations may also be used in this prime/boost approach.

The invention also provides an immunogenic composition comprising antigens from H5 viruses in at least two different clades. Useful combinations of two clades include, but are not limited to:

| | | | | | | | | | | | | | |
|---|---|---|---|---|---|---|---|---|---|---|---|---|---|
| First | 1 | 1 | 1 | 1 | 1 | 1 | 1 | 1 | 2 | 2 | 1 | 1 | 1 |
| Second | 2 | 3 | 4 | 5 | 6 | 7 | 8 | 9 | 4 | 7 | 2.1 | 2.2 | 2.3 |

The Influenza Virus Antigen

Vaccines used with the invention include an antigen from an influenza A virus having a H5 hemagglutinin subtype. The vaccine will comprise a protein comprising at least one H5 hemagglutinin epitope e.g. the vaccine will comprise viral hemagglutinin from a H5 virus.

Preferred vaccines of the invention also include a protein comprising at least one influenza virus neuraminidase epitope e.g. the vaccine will include viral neuraminidase from a H5 virus. The invention may protect against one or more of influenza A virus NA subtypes N1, N2, N3, N4, N5, N6, N7, N8 or N9, but it will usually be against N1 (i.e. a H5N1 virus) or N3 (i.e. a H5N3 virus). The first clade and second clade may have the same NA subtype (e.g. both N1 or both N3) or different NA subtypes (e.g. N1 then N3, or N3 then N1, etc.). If only one of the priming and boosting doses includes neuraminidase, it may be the priming dose.

The antigen will typically be prepared from influenza virions but, as an alternative, antigens such as haemagglutinin and neuraminidase can be expressed in a recombinant host (e.g. in an insect cell line using a baculovirus vector) and used in purified form [4, 5, 6] or in the form of virus-like particles (VLPs; e.g. see references 7 and 8). In general, however, antigens will be from virions.

The antigen may take the form of a live virus or, more preferably, an inactivated virus. Chemical means for inactivating a virus include treatment with an effective amount of one or more of the following agents: detergents, formaldehyde, formalin, β-propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation.

Where an inactivated virus is used, the vaccine may comprise whole virion, split virion, or purified surface antigens (including hemagglutinin and, usually, also including neuraminidase). The DARONRIX™ H5N1 product is a whole virion inactivated vaccine. The PREPANDRIX™ H5N1 product is a split virion inactivated vaccine. Split virion and purified surface antigens (i.e. subvirion vaccines) are particularly useful with the invention.

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses are well known in the art e.g. see refs. 9-14, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™, FOCETRIA™ and INFLUVAC™ products are subunit vaccines.

Influenza antigens can also be presented in the form of virosomes [15] (nucleic acid free viral-like liposomal particles), as in the INFLEXAL V™ and INVAVAC™ products, but it is preferred not to use virosomes with the present invention. Thus, in some embodiments, the influenza antigen is not in the form of a virosome.

The strain from which the virus is prepared will typically be an avian influenza virus or a human influenza virus. Usually it will be capable of infecting humans, but in some cases a strain may be used that cannot infect humans e.g. an avian strain that may later acquire the ability to infect humans. The strain may be a HPAI (highly pathogenic avian influenza) strain [16].

The influenza virus may be attenuated. The influenza virus may be temperature-sensitive. The influenza virus may be cold-adapted. These three features are particularly useful when using live virus as an antigen.

The influenza virus may be resistant to antiviral therapy (e.g. resistant to oseltamivir [17] and/or zanamivir).

Compositions of the invention may include antigen(s) from one or more (e.g. 1, 2, 3, 4 or more) influenza virus strains, including influenza A virus and/or influenza B virus, provided that they include antigen from at least one H5 strain. Thus a composition may include antigen from one or more strains characteristics of a normal seasonal vaccine plus at least one H5 strain e.g. a 4-valent vaccine with three influenza A strains (H1N1 and H3N2, plus a H5 strain e.g. H5N1), and one influenza B strain. In other embodiments if may include antigen from at least two H5 strains, and optionally a H1 strain and/or a H3 strain and/or an influenza B virus strain. Where a vaccine includes more than one strain of influenza, the different strains are typically grown separately and are mixed after the viruses have been harvested and antigens have been prepared. Thus a process of the invention may include the step of mixing antigens from more than one influenza strain.

The influenza virus may be a reassortant strain, and may have been obtained by reverse genetics techniques. Reverse genetics techniques [e.g. 18-22] allow influenza viruses with desired genome segments to be prepared in vitro using plasmids. Typically, it involves expressing (a) DNA molecules that encode desired viral RNA molecules e.g. from polI promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred [23-25], and these methods will also involve the use of plasmids to express all or some (e.g. just the PB1, PB2, PA and NP proteins) of the viral proteins, with up to 12 plasmids being used in some methods. If canine cells are used, a canine polI promoter may be used [26].

To reduce the number of plasmids needed, one approach [27] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). Preferred aspects of the reference 27 method involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters [28]. For instance, promoters for the SP6, T3 or T7 polymerases can conveniently be used. Because of the species-specificity of polI promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template [29,30].

An influenza A virus may include one or more RNA segments from a A/PR/8/34 virus (typically 6 segments from A/PR/8/34, with the HA and N segments being from a vaccine strain, i.e. a 6:2 reassortant), particularly when viruses are grown in eggs. It may also include one or more RNA segments from a A/WSN/33 virus, or from any other virus strain useful for generating reassortant viruses for vaccine preparation. Typically, the invention protects against a strain that is capable of human-to-human transmission, and so the strain's genome will usually include at least one RNA segment that originated in a mammalian (e.g. in a human) influenza virus. It may include NS segment that originated in an avian influenza virus.

The viruses used as the source of the antigens can be grown either on eggs or on cell culture. The current standard method for influenza virus growth uses specific pathogen-free (SPF) embryonated hen eggs, with virus being purified from the egg contents (allantoic fluid). More recently, however, viruses have been grown in animal cell culture and, for reasons of speed and patient allergies, this growth method is preferred. If egg-based viral growth is used then one or more amino acids may be introduced into the allantoid fluid of the egg together with the virus [14].

When cell culture is used, the viral growth substrate will typically be a cell line of mammalian origin. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells [31-34], derived from Madin Darby canine kidney; Vero cells [35-37], derived from African green monkey (*Cercopithecus aethiops*) kidney; or PER.C6 cells [38], derived from human embryonic retinoblasts. These cell lines are widely available e.g. from the American Type Cell Culture (ATCC) collection, from the Coriell Cell Repositories, or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 39-41], including cell lines derived from ducks (e.g. duck retina) or hens. Examples of avian cell lines include avian embryonic stem cells [39,42] and duck retina cells [40]. Suitable avian embryonic stem cells, include the EBx cell line derived from chicken embryonic stem cells, EB45, EB14, and EB14-074 [43]. Chicken embryo fibroblasts (CEF) may also be used.

The most preferred cell lines for growing influenza viruses are MDCK cell lines. The original MDCK cell line is available from the ATCC as CCL-34, but derivatives of this cell line may also be used. For instance, reference 31 discloses a MDCK cell line that was adapted for growth in suspension culture ('MDCK 33016', deposited as DSM ACC 2219). Similarly, reference 44 discloses a MDCK-derived cell line that grows in suspension in serum-free culture ('B-702', deposited as FERM BP-7449). Reference 45 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 46 discloses MDCK cell lines with high susceptibility to infection, including 'MDCK.5F1' cells (ATCC CRL-12042). Any of these MDCK cell lines can be used.

Where virus has been grown on a mammalian cell line then the composition will advantageously be free from egg proteins (e.g. ovalbumin and ovomucoid) and from chicken DNA, thereby reducing allergenicity.

Where virus has been grown on a cell line then the culture for growth, and also the viral inoculum used to start the culture, will preferably be free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [47]. Absence of herpes simplex viruses is particularly preferred.

For growth on a cell line, such as on MDCK cells, virus may be grown on cells in suspension [48-50] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [51] during viral replication e.g. 30-36° C.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may, be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

Haemagglutinin (HA) is the main immunogen in inactivated influenza vaccines, and vaccine doses are standardised by reference to HA levels, typically as measured by a single radial immunodiffusion (STUD) assay. Current vaccines typically contain about 15 μg of HA per strain, although lower doses are also used e.g. for children, or in pandemic situations. Fractional doses such as ½ (i.e. 7.5 μg HA per strain, as in FOCETRIA™), ¼ (i.e. 3.75 μg per strain, as in PREPANDRIX™) and ⅛ have been used [52,53], as have higher doses (e.g. 3× or 9× doses [54,55]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 3.75, about 1.9, about 1.5, etc. μg per strain. An equal HA mass per strain is typical. For compositions including HA from strains in different H5 clades, it is useful to include 3.75 μg, 7.5 μg, or 15 μg per strain (e.g. 2×3.75 μg, giving a total of 7.5 μg HA, typically in combination with an adjuvant such as a squalene-in-water emulsion). Lower doses (i.e. <15 μg/dose) are most useful when an adjuvant is present in the vaccine, as with the invention. Although doses as high as 90 μg have been used in some studies (e.g. reference 56), compositions of the invention (particularly in the boosting dose) will usually include 15 μg/dose or less.

For live vaccines, dosing is measured by median tissue culture infectious dose ($TCID_{50}$) rather than HA content, and a $TCID_{50}$ of between $10^6$ and $10^8$ (preferably between $10^{65}$-$10^{75}$) per strain is typical.

HA used with the invention may be a natural HA as found in a virus, or may have been modified. For instance, it is known to modify HA to remove determinants (e.g. hyper-basic regions around the cleavage site between HA1 and HA2) that cause a virus to be highly pathogenic in avian species, as these determinants can otherwise prevent a virus from being grown in eggs.

Compositions of the invention may include detergent e.g. a polyoxyethylene sorbitan ester surfactant (known as 'Tweens' e.g. polysorbate 80), an octoxynol (such as octoxynol-9 (Triton X-100) or 10, or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may included less than 1 mg/ml of each of octoxynol-10, α-tocopheryl hydrogen succinate and polysorbate 80. Other residual components in trace amounts could be antibiotics (e.g. neomycin, kanamycin, polymyxin B).

Host Cell DNA

Where virus has been grown on a cell line then it is standard practice to minimize the amount of residual cell line DNA in the final vaccine, in order to minimize any oncogenic activity of the DNA. Thus, where virus has been grown on a cell line, the composition preferably contains less than 10 ng (preferably less than 1 ng, and more preferably less than 100 pg) of residual host cell DNA per dose, although trace amounts of host cell DNA may be present. It is preferred that the average length of any residual host cell DNA is less than 500 bp e.g. less than 400 bp, less than 300 bp, less than 200 bp, less than 100 bp, etc. In general, the host cell DNA that it is desirable to exclude from compositions of the invention is DNA that is longer than 100 bp.

Measurement of residual host cell DNA is now a routine regulatory requirement for biologicals and is within the normal capabilities of the skilled person. The assay used to measure DNA will typically be a validated assay [57,58]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three principle techniques for DNA quantification can be used: hybridization methods, such as Southern blots or slot blots [59]; immunoassay methods, such as the Threshold™ System [60]; and quantitative PCR [61]. These methods are all familiar to the skilled person, although the precise characteristics of each method may depend on the host cell in question e.g. the choice of probes for hybridization, the choice of primers and/or probes for amplification, etc. The Threshold™ system from Molecular Devices is a quantitative assay for picogram levels of total DNA, and has been used for monitoring levels of contaminating DNA in biopharmaceuticals [60]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 62.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 63 & 64, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [65].

Vaccines containing <10 ng (e.g. <1 ng, <100 pg) host cell DNA per 15 μg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 μg of haemagglutinin are more preferred, as are vaccines containing <10 ng (e.g. <1 ng, <100 pg) host cell DNA per 0.5 ml volume.

Adjuvant(s)

A composition of the invention may include an adjuvant to enhance the immune responses (humoral and/or cellular) elicited in a patient who receives the composition.

It is preferred that the first clade vaccine and the second clade vaccine are both adjuvanted vaccines. They may use the same adjuvant or different adjuvants. If only one of the two vaccines is adjuvanted then preferably it is the second.

Suitable adjuvants for use with the invention include, but are not limited to:

A mineral-containing composition, including calcium salts and aluminum salts (or mixtures thereof). Calcium salts include calcium phosphate (e.g. the "CAP" particles disclosed in ref. 66). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [67]. Aluminum salt adjuvants are described in more detail below.

An oil-in-water emulsion, as described in more detail below.

An immunostimulatory oligonucleotide, as described in more detail below.

3-O-deacylated monophosphoryl lipid A ('3dMPL', also known as 'MPL™'), as described in more detail below.

An imidazoquinoline compound, such as Imiquimod ("R-837") [68,69], Resiquimod ("R-848") [70], and their analogs; and salts thereof (e.g. the hydrochloride salts). Further details about immunostimulatory imidazoquinolines can be found in references 71 to 75.

A thiosemicarbazone compound, such as those disclosed in reference 76. Methods of formulating, manufacturing, and screening for active compounds are also described in reference 76. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

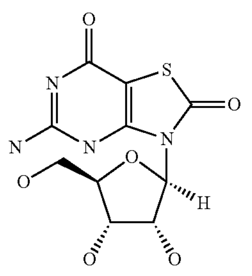 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 77 to 79; (f) a compound having the formula:

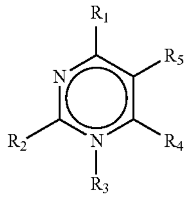

wherein:

$R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

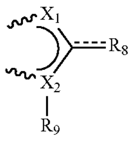

$R_{4-5}$ the binding being achieved at the bonds indicated by a $X_1$ and $X_2$ are each independently N, C, O, or S;

$R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—($C_{1-6}$ alkyl), —$S(O)_pR_e$, or —C(O)—$R_d$;

$R_9$ is H, $C_{1-6}$ alkyl, substituted $C_{1-6}$ alkyl, heterocyclyl, substituted heterocyclyl or $R_{9a}$, wherein $R_{9a}$ is:

$R_{9a}$

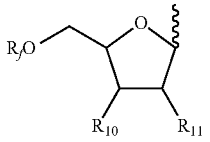

the binding being achieved at the bond indicated by a ∿∿∿

$R_{10}$ and $R_{11}$ are each independently H, halo, $C_{1-6}$ alkoxy, substituted $C_{1-6}$ alkoxy, —$NR_aR_b$, or —OH;

each $R_a$ and $R_b$ is independently H, $C_{1-6}$ alkyl, substituted $C_{1-6}$ alkyl, —C(O)$R_d$, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, —$NH_2$, —NH($C_{1-6}$ alkyl), —NH(substituted $C_{1-6}$ alkyl), —N($C_{1-6}$ alkyl)$_2$, —N(substituted $C_{1-6}$ alkyl)$_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, —C(O)$R_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

A tryptanthrin compound, such as those disclosed in reference 80. Methods of formulating, manufacturing, and screening for active compounds are also described in reference 80. The thiosemicarbazones are particularly effective in the stimulation of human peripheral blood mononuclear cells for the production of cytokines, such as TNF-α.

Loxoribine (7-allyl-8-oxoguanosine) [81].

Compounds disclosed in reference 82, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [83,84], Hydrapthalamide compounds, Benzophenone compounds, Isoxazole compounds, Sterol compounds, Quinazilinone compounds, Pyrrole compounds [85], Anthraquinone compounds, Quinoxaline compounds, Triazine compounds, Pyrazalopyrimidine compounds, and Benzazole compounds [86].

Compounds disclosed in reference 87, including 3,4-di(1H-indol-3-yl)-1H-pyrrole-2,5-diones, staurosporine analogs, derivatized pyridazines, chromen-4-ones, indolinones, quinazolines, and nucleoside analogs.

An aminoalkyl glucosaminide phosphate derivative, such as RC-529 [88,89].

A phosphazene, such as poly[di(carboxylatophenoxy) phosphazene] ("PCPP") as described, for example, in references 90 and 91.

Small molecule immunopotentiators (SMIPs) such as:

N2-methyl-1-(2-methylpropyl)-1H-imidazo[4,5-c]quinoline-2,4-diamine

N2,N2-dimethyl-1-(2-methylpropyl)-1H-imidazo[4,5-c]quinoline-2,4-diamine

N2-ethyl-N2-methyl-1-(2-methylpropyl)-1H-imidazo[4,5-c]quinoline-2,4-diamine

N2-methyl-1-(2-methylpropyl)-N2-propyl-1H-imidazo[4,5-c]quinoline-2,4-diamine 1-(2-methylpropyl)-N2-propyl-1H-imidazo[4,5-c]quinoline-2,4-diamine N2-butyl-1-(2-methylpropyl)-1H-imidazo[4,5-c]quinoline-2,4-diamine N2-butyl-N2-methyl-1-(2-methylpropyl)-1H-imidazo[4,5-c]quinoline-2,4-diamine N2-methyl-1-(2-methylpropyl)-N2-pentyl-1H-imidazo[4,5-c]quinoline-2,4-diamine N2-methyl-1-(2-methylpropyl)-N2-prop-2-enyl-1H-imidazo[4,5-c]quinoline-2,4-diamine 1-(2-methylpropyl)-2-[(phenylmethyl)thio]-1H-imidazo[4,5-c]quinolin-4-amine 1-(2-methylpropyl)-2-(propylthio)-1H-imidazo[4,5-c]quinolin-4-amine 2-[[4-amino-1-(2-methylpropyl)-1H-imidazo[4,5-c]quinolin-2-yl](methy)amino]ethanol 2-[[4-amino-1-(2-methylpropyl)-1H-imidazo[4,5-c]quinolin-2-yl](methyl)amino]ethyl acetate 4-amino-1-(2-methylpropyl)-1,3-dihydro-2H-imidazo[4,5-c]quinolin-2-one N2-butyl-1-(2-methylpropyl)-N4,N4-bis(phenylmethyl)-1H-imidazo[4,5-c]quinoline-2,4-diamine N2-butyl-N2-methyl-1-(2-methylpropyl)-N4,N4-bis(phenylmethyl)-1H-imidazo[4,5-c]quinoline-2,4-diamine N2-methyl-1-(2-methylpropyl)-N4,N4-bis(phenylmethyl)-1H-imidazo[4,5-c]quinoline-2,4-diamine N2,N2-dimethyl-1-(2-methylpropyl)-N4,N4-bis(phenylmethyl)-1H-imidazo[4,5-c]quinoline-2,4-diamine 1-{4-amino-2-[methyl(propyl)amino]-1H-imidazo[4,5-c]quinolin-1-yl}-2-methylpropan-2-ol 1-[4-amino-2-(propylamino)-1H-imidazo[4,5-c]quinolin-1-yl]-2-methylpropan-2-ol N4,N4-dibenzyl-1-(2-methoxy-2-methylpropyl)-N2-propyl-1H-imidazo[4,5-c]quinoline-2,4-diamine.

Saponins [chapter 22 of ref. 133], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 92. Saponin formulations may also comprise a sterol, such as cholesterol [93]. Combinations of saponins and cholesterols can be used to form unique particles called immunostimulating complexs (ISCOMs) [chapter 23 of ref 133]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 93-95. Optionally, the ISCOMS may be devoid of additional detergent [96]. A review of the development of saponin based adjuvants can be found in refs. 97 & 98.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 [99]. The use of detoxified ADP-ribosylating toxins as mucosal adjuvants is described in ref. 100 and as parenteral adjuvants in ref 101.

Bioadhesives and mucoadhesives, such as esterified hyaluronic acid microspheres [102] or chitosan and its derivatives [103].

Microparticles (i.e. a particle of ~100 nm to ~150 μm in diameter, more preferably ~200 nm to ~30 μm in diameter, or ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of ref 133). Examples of liposome formulations suitable for use as adjuvants are described in refs. 104-106.

Polyoxyethylene ethers and polyoxyethylene esters [107]. Such formulations further include polyoxyethylene sorbitan ester surfactants in combination with an octoxynol [108] as well as polyoxyethylene alkyl ethers or ester surfactants in combination with at least one additional non-ionic surfactant such as an octoxynol [109]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

An outer membrane protein proteosome preparation prepared from a first Gram-negative bacterium in combination with a liposaccharide (LPS) preparation derived from a second Gram-negative bacterium, wherein the outer membrane protein proteosome and LPS preparations form a stable non-covalent adjuvant complex. Such complexes include "IVX-908", a complex comprised of *Neisseria meningitidis* outer membrane and LPS. They have been used as adjuvants for influenza vaccines [110].

A polyoxidonium polymer [111,112] or other N-oxidized polyethylene-piperazine derivative.

Methyl inosine 5'-monophosphate ("MIMP") [113].

A polyhydroxlated pyrrolizidine compound [114], such as one having formula:

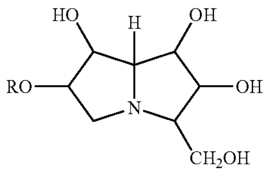

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide [115-122] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin [123] or derivative thereof, such as algammulin.

A compound of formula I, II or III, or a salt thereof:

I

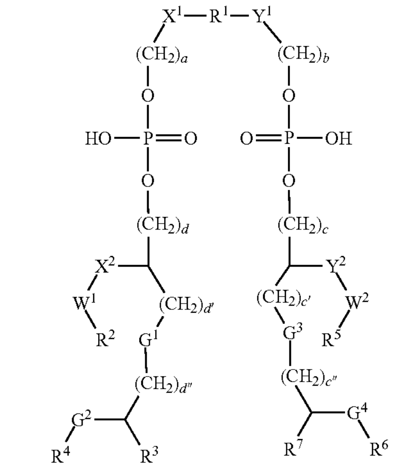

II

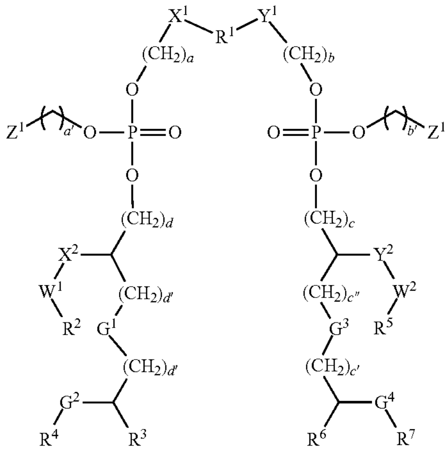

-continued

III

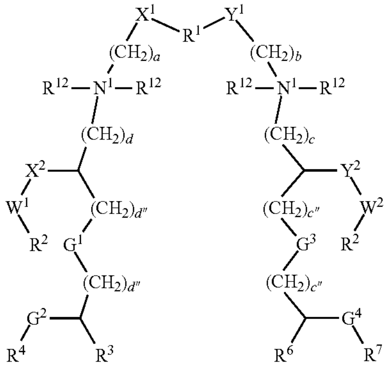

as defined in reference 124, such as 'ER 803058', 'ER 803732', 'ER 804053', ER 804058', 'ER 804059', 'ER 804442', 'ER 804680', 'ER 804764', ER 803022 or 'ER 804057' e.g.:

Derivatives of lipid A from *Escherichia coli* such as OM-174 (described in refs. 125 & 126).

A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE:DOPE"). Formulations containing (±)-N-(3-aminopropyl)-N,N-dimethyl-2,3-bis(syn-9-tetradeceneyloxy)-1-propanaminium salts are preferred [127].

Compounds containing lipids linked to a phosphate-containing acyclic backbone, such as the TLR4 antagonist E5564 [128,129]:

ER-803022:

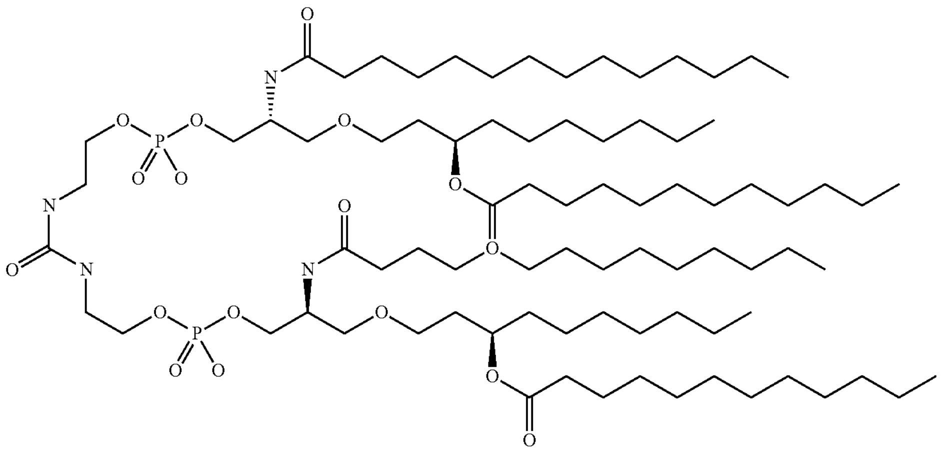

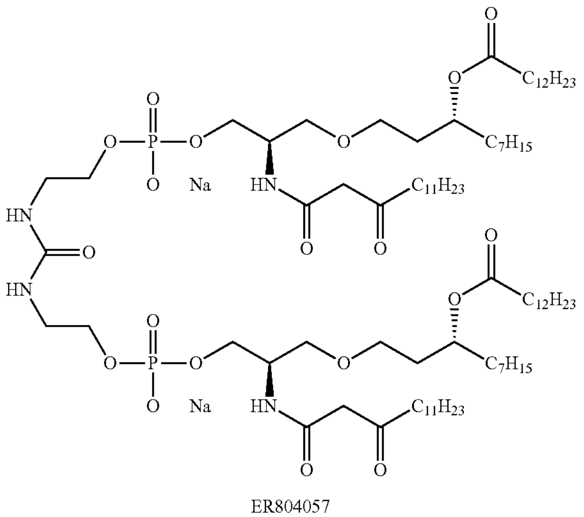

ER804057

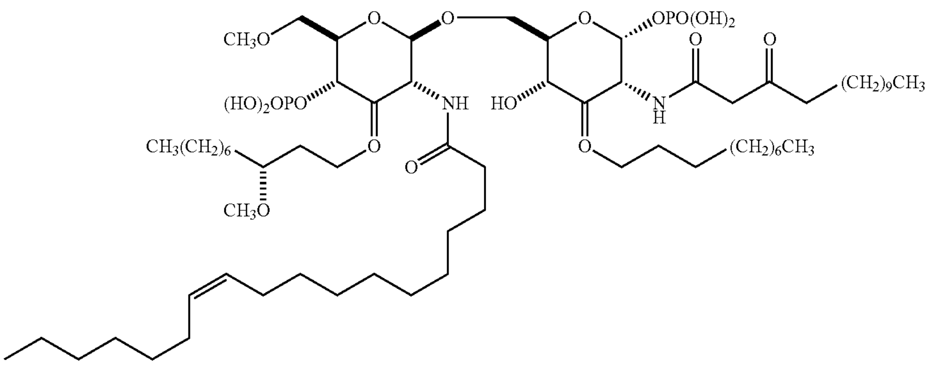

These and other adjuvant-active substances are discussed in more detail in references 133 & 134.

The adjuvant(s) for use in the present invention may be modulators and/or agonists of Toll-Like Receptors (TLR). For example, they may be agonists of one or more of the human TLR1, TLR2, TLR3, TLR4, TLR7, TLR8, and/or TLR9 proteins. Preferred agents are agonists of TLR7 (e.g. imidazoquinolines) and/or TLR9 (e.g. CpG oligonucleotides). These agents are useful for activating innate immunity pathways.

A single vaccine may include two or more of said adjuvants.

Antigens and adjuvants in a composition will typically be in admixture.

Aluminum Salt Adjuvants

The adjuvants known as aluminum hydroxide and aluminum phosphate may be used. These names are conventional, but are used for convenience only, as neither is a precise description of the actual chemical compound which is present (e.g. see chapter 9 of reference 133). The invention can use any of the "hydroxide" or "phosphate" adjuvants that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ [chapter 9 of ref. 133]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4$/Al molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls [ch. 9 of ref. 133]. The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate, as in DARONRIX™. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Oil-In-Water Emulsion Adjuvants

Oil-in-water emulsions have been found to be particularly suitable for use in adjuvanting influenza virus vaccines. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [130-132], as described in more detail in Chapter 10 of ref. 133 and chapter 12 of ref 134. The MF59 emulsion advantageously includes citrate ions e.g. 10 mM sodium citrate buffer.
- An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 (e.g. 0.90) as this provides a more stable emulsion. Squalene and Tween 80 may be present volume ratio of about 5:2, or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [135] (0.05-1% Thr-MDP, 5% squalane, 2.5% Pluronic L121 and 0.2% polysorbate 80). It can also be used without the Thr-MDP, as in the "AF" adjuvant [136] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [137]. The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. As described in reference 138, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 139, produced by addition of aliphatic amine to desacylsaponin via the carboxyl group of glucuronic acid), dimethyldioctadecylammonium bromide and/or N,N-dioctadecyl-N, N-bis(2-hydroxyethyl)propanediamine.

An emulsion in which a saponin (e.g. QuilA or QS21) and a sterol (e.g. a cholesterol) are associated as helical micelles [140].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [141].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [141].

Preferred oil-in-water emulsions of the invention comprise squalene.

The emulsions may be mixed with antigen extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1. If emulsion and antigen are stored separately in a multidose kit then the product may be presented as a vial containing 2.5 ml of emulsion and a vial containing 2.5 ml of aqueous antigen, for mixing to give 5 ml of adjuvanted vaccine e.g. 10×0.5 ml doses.

After the antigen and adjuvant have been mixed, haemagglutinin antigen will generally remain in aqueous solution but may distribute itself around the oil/water interface. In general, little if any haemagglutinin will enter the oil phase of the emulsion.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group [142]. They also have antioxidant properties that may help to stabilize the emulsions [143]. A preferred α-tocopherol is DL-α-tocopherol, and the preferred salt of this tocopherol is the succinate. The succinate salt has been found to cooperate with TNF-related ligands in vivo. Moreover, α-tocopherol succinate is known to be compatible with influenza vaccines and to be a useful preservative as an alternative to mercurial compounds [13].

Immunostimulatory Oligonucleotides

Immunostimulatory oligonucleotides can include nucleotide modifications/analogs such as phosphorothioate modifications and can be double-stranded or (except for RNA) single-stranded. References 144, 145 and 146 disclose possible analog substitutions e.g. replacement of guanosine with 2'-deoxy-7-deazaguanosine. The adjuvant effect of CpG oligonucleotides is further discussed in refs. 147-152. A CpG sequence may be directed to TLR9, such as the motif GTCGTT or TTCGTT [153]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 154-156. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 153 & 157-159. A useful CpG adjuvant is CpG7909, also known as ProMune™ (Coley Pharmaceutical Group, Inc.).

As an alternative, or in addition, to using CpG sequences, TpG sequences can be used [160]. These oligonucleotides may be free from unmethylated CpG motifs.

The immunostimulatory oligonucleotide may be pyrimidine-rich. For example, it may comprise more than one consecutive thymidine nucleotide (e.g. TTTT, as disclosed in ref. 160), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 160), and/or it may have a nucleotide composition with >25% cytosine (e.g. >35%, >40%, >50%, >60%, >80%, etc.). These oligonucleotides may be free from unmethylated CpG motifs.

Immunostimulatory oligonucleotides will typically comprise at least 20 nucleotides. They may comprise fewer than 100 nucleotides.

A particularly useful adjuvant based around immunostimulatory oligonucleotides is known as IC31™ [161]. Thus an adjuvant used with the invention may comprise a mixture of (i) an oligonucleotide (e.g. between 15-40 nucleotides) including at least one (and preferably multiple) CpI motifs, and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-$(IC)_{13}$-3' (SEQ ID NO: 14). The polycationic polymer may be a peptide comprising 11-mer amino acid sequence KLKLLLLLKLK (SEQ ID NO: 15).

3 de-O-Acylated Monophosphoryl Lipid A

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF (see also ref. 162). Preparation of 3dMPL was originally described in reference 163.

3dMPL can take the form of a mixture of related molecules, varying by their acylation (e.g. having 3, 4, 5 or 6 acyl chains, which may be of different lengths). The two glucosamine (also known as 2-deoxy-2-amino-glucose) monosaccharides are N-acylated at their 2-position carbons (i.e. at positions 2 and 2'), and there is also O-acylation at the 3' position. The group attached to carbon 2 has formula $-NH-CO-CH_2-CR^1R^{1'}$. The group attached to carbon 2' has formula $-NH-CO-CH_2-CR^2R^{2'}$. The group attached to carbon 3' has formula $-O-CO-CH_2-CR^3R^{3'}$. A representative structure is:

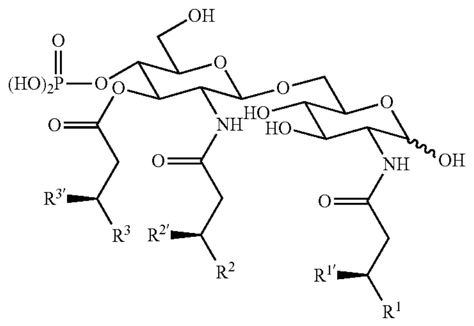

Groups $R^1$, $R^2$ and $R^3$ are each independently $-(CH_2)_n-CH_3$. The value of n is preferably between 8 and 16, more preferably between 9 and 12, and is most preferably 10.

Groups $R^{1'}$, $R^{2'}$ and $R^{3'}$ can each independently be: (a) —H; (b) —OH; or (c) $-O-CO-R^4$, where $R^4$ is either —H or $-(CH_2)_m-CH_3$, wherein the value of m is preferably between 8 and 16, and is more preferably 10, 12 or 14. At the 2 position, m is preferably 14. At the 2' position, m is preferably 10. At the 3' position, m is preferably 12. Groups $R^{1'}$, $R^{2'}$ and $R^{3'}$ are thus preferably —O-acyl groups from dodecanoic acid, tetradecanoic acid or hexadecanoic acid.

When all of $R^{1'}$, $R^{2'}$ and $R^{3'}$ are —H then the 3dMPL has only 3 acyl chains (one on each of positions 2, 2' and 3'). When only two of $R^{1'}$, $R^{2'}$ and $R^{3'}$ are —H then the 3dMPL can have 4 acyl chains. When only one of $R^{1'}$, $R^{2'}$ and $R^{3'}$ is —H then the 3dMPL can have 5 acyl chains. When none of $R^{1'}$, $R^{2'}$ and $R^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL e.g. ≥20%, ≥30%, ≥40%, ≥50% or more. 3dMPL with 6 acyl chains has been found to be the most adjuvant-active form.

Thus the most preferred form of 3dMPL for inclusion in compositions of the invention is:

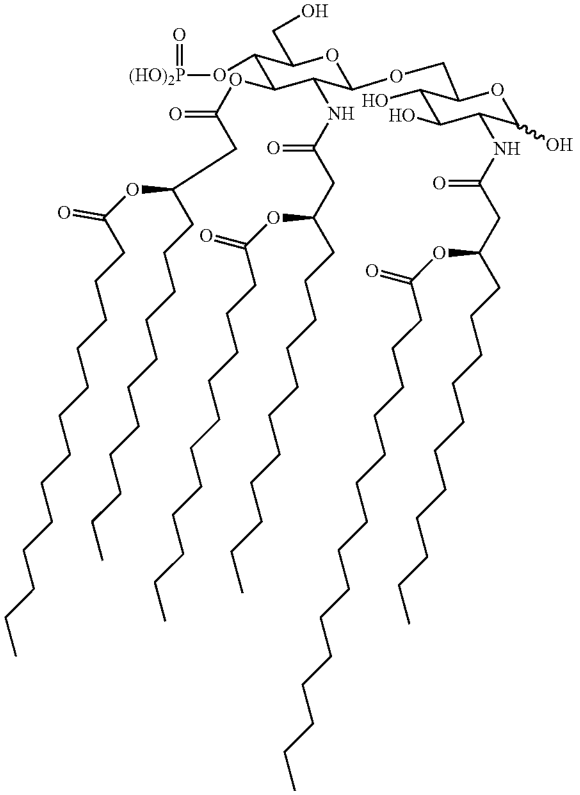

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [164]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g. ≥60%, ≥70%, ≥80%, ≥90%, or more) of the particles will have a diameter within the range x±25%.

3dMPL can advantageously be used in combination with an oil-in-water emulsion. Substantially all of the 3dMPL may be located in the aqueous phase of the emulsion.

The 3dMPL can be used on its own, or in combination with one or more further compounds. For example, it is known to use 3dMPL in combination with the QS21 saponin [165] (including in an oil-in-water emulsion [166]), with an immunostimulatory oligonucleotide, with both QS21 and an immunostimulatory oligonucleotide, with aluminum phosphate [167], with aluminum hydroxide [168], or with both aluminum phosphate and aluminum hydroxide.

Pharmaceutical Compositions

Compositions of the invention are pharmaceutically acceptable and are typically in aqueous form. They may include components in addition to the antigen (and, where applicable, the adjuvant) e.g. they typically include one or more pharmaceutical carrier(s) and/or excipient(s). A thorough discussion of such components is available in reference 169.

The composition may include preservatives such as thiomersal (e.g at 10 μg/ml) or 2-phenoxyethanol. It is preferred, however, that the vaccine should be substantially free from (i.e. less than 5 μg/ml) mercurial material e.g. thiomersal-free [13,170]. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [171], but keeping osmolality in this range is nevertheless preferred.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. between 6.5 and 7.5, between 7.0 and 7.8. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit e.g. for 10 doses). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered, for example to children (e.g. up to 36 months of age).

Compositions and kits are preferably stored at between 2° C. and 8° C. They should not be frozen. They should ideally be kept out of direct light.

Kits of the Invention

The invention includes kits containing more than one composition of the invention e.g. a priming composition and a boosting composition. The two kit components will be kept separately, as they are administered to a patient at substantially different times.

Each individual vaccine in a kit may be ready for use, or may be ready for extemporaneous preparation at the time of delivery. This extemporaneous arrangement allows the adjuvant and the antigen to be kept separately until the time of use, which is particularly useful when using an oil-in-water emulsion adjuvant.

Where a vaccine is prepared extemporaneously, its components are physically separate from each other within the kit, and this separation can be achieved in various ways. For instance, the two components may be in two separate containers, such as vials e.g. an antigen vial and an emulsion vial. The contents of the two vials can then be mixed e.g. by removing the contents of one vial and adding them to the other vial, or by separately removing the contents of both vials and mixing them in a third container. In a preferred arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two components of a vaccine are held together but separately in the same syringe e.g. a dual-chamber syringe, such as those disclosed in references 172-179 etc. When the syringe is actuated (e.g. during administration to a patient) then the contents of the two chambers are mixed. This arrangement avoids the need for a separate mixing step at the time of use.

Where a vaccine is prepared extemporaneously, its components will generally be in aqueous form. In some arrangements, a component (typically the antigen component rather than the adjuvant component) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilised antigen component in a vial.

Packaging of Compositions or Kit Components

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a composition/component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™. Butyl rubber is also a suitable material for the stoppers of vials e.g. in multidose kits.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

Compositions of the invention are suitable for administration to human patients, and the invention provides a method of raising an immune response in a patient, comprising the step of administering a composition of the invention to the patient.

The invention also provides a kit or composition of the invention for use in medicine e.g. for use in raising an immune response in a patient.

The invention also provides an influenza virus antigen from a first clade of H5 influenza A virus and an influenza virus antigen from a second clade of H5 influenza A virus, wherein the first and second clades are different from each other, for simultaneous separate or sequential administration.

The invention also provides an influenza virus antigen from a first clade of H5 influenza A virus and an influenza virus antigen from a second clade of H5 influenza A virus, wherein the first and second clades are different from each other, for combined use in therapy.

The invention also provides a combination of an influenza virus antigen from a first clade of H5 influenza A virus and an influenza virus antigen from a second clade of H5 influenza A virus, wherein the first and second clades are different from each other, for use in therapy.

The invention also provides the use of an influenza virus antigen from a first clade of H5 influenza A virus in the manufacture of a medicament for raising an immune response in a patient, wherein the medicament is prepared for administration with (or is administered with) an influenza virus antigen from a second clade of H5 influenza A virus, wherein the first and second clades are different from each other.

The invention also provides the use of (i) an influenza virus antigen from a first clade of H5 influenza A virus and (ii) an influenza virus antigen from a second clade of H5 influenza A virus, wherein the first and second clades are different from each other, in the manufacture of a medicament for raising an immune response in a patient.

The invention also provides the use of an influenza virus antigen from a second clade of H5 influenza A virus in the manufacture of a medicament for raising an immune response in a patient who has previously been immunized with influenza virus antigen from a first clade of H5 influenza A virus, wherein the first and second clades are different. These pre-immunized patients are distinguished from the general population in various ways e.g. by the presence of memory B cells that will respond to re-immunization with H5 hemagglutinin.

The invention also provides the use of an influenza virus antigen from a first clade of H5 influenza A virus in the manufacture of a medicament for raising an immune response in a patient, wherein the patient will later be immunized with influenza virus antigen from a second clade of H5 influenza A virus, wherein the first and second clades are different.

The immune response raised according to the invention will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [180]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [181-183], oral [184], intradermal [185,186], transcutaneous, transdermal [187], etc.

Vaccines of the invention may be used to treat both children and adults. Influenza vaccines are currently recommended for use in pediatric and adult immunisation, from the age of 6 months. Thus the patient may be less than 1 year old, 1-5 years old, 5-15 years old, 15-55 years old, or at least 55 years old. Preferred patients for receiving the vaccines are the elderly (e.g. ≥50 years old, ≥60 years old, preferably ≥65 years), the young (e.g. ≤5 years old), hospitalised patients, healthcare workers, armed service and military personnel, pregnant women, the chronically ill, immunodeficient patients, patients who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (≥60 years), these criteria are: (1) ≥60% seroprotection; (2) ≥30% seroconversion; and/or (3) a GMT increase of ≥2-fold. These criteria are based on open label studies with at least 50 patients.

In prime-boost embodiments of the invention, a patient is subjected to a multiple dose schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Where the invention involves immunizing (boosting) a patient who has previously been immunized against a different H5 clade, the booster dose may be given several months after the previous dose e.g. at least 6 months, 9 months, 12 months, 18 months, 24 months, 36 months, 48 months, 60 months or more.

In embodiments where a composition includes HA from more than one clade of H5 influenza A virus, this composition may be administered by a single dose schedule or a multiple dose schedule. Administration of more than one dose (typically two doses) is particularly useful in immunologically naïve patients e.g. for people who have never received an influenza vaccine before, or for vaccinating against a new HA subtype such as H5. As above, multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Compositions of the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine or a meningococcal vaccine is particularly useful in elderly patients.

Similarly, compositions of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3 (1-ethylpropoxy)-1-cyclohexene-1-carboxylic acid, ethyl ester, phosphate (1:1), also known as oseltamivir phosphate (TAMIFLU™).

FURTHER EMBODIMENTS

In addition to the above embodiments, the invention also provides an immunogenic composition comprising (a) hemagglutinin antigen from at least one strain (e.g. 1, 2, 3, 4, 5 or 6 different strains) of H5 influenza A virus and (b) hemagglutinin antigen from (i) at least one strain of a H7 influenza A virus and/or (ii) at least one strain of a H9 influenza A virus. Thus the vaccine may include hemagglutinin H5+H7, H5+H9 or H5+H7+H9. It is preferred to include hemagglutinin antigen from at least two strains (e.g. 2, 3, 4, 5 or 6 different strains) of H5 influenza A virus, in which case these strains are preferably in different clades as described herein. A bivalent combination with hemagglutinin from only one H5 strain and one H7 strain is not preferred [188].

The invention also provides an immunogenic composition comprising (a) hemagglutinin antigen from at least one strain (e.g. 1, 2, 3, 4, 5 or 6 different strains) of H5 influenza A virus and (b) hemagglutinin antigen from at least two of influenza A virus subtypes H2, H4, H6, H7, H8, H9, H10, H11, H12, H13, H14, H15 and/or H16. If hemagglutinin from more than one H5 strain is included then these strains are preferably in different clades as described herein.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

MODES FOR CARRYING OUT THE INVENTION

Human Study I

Figure 1:
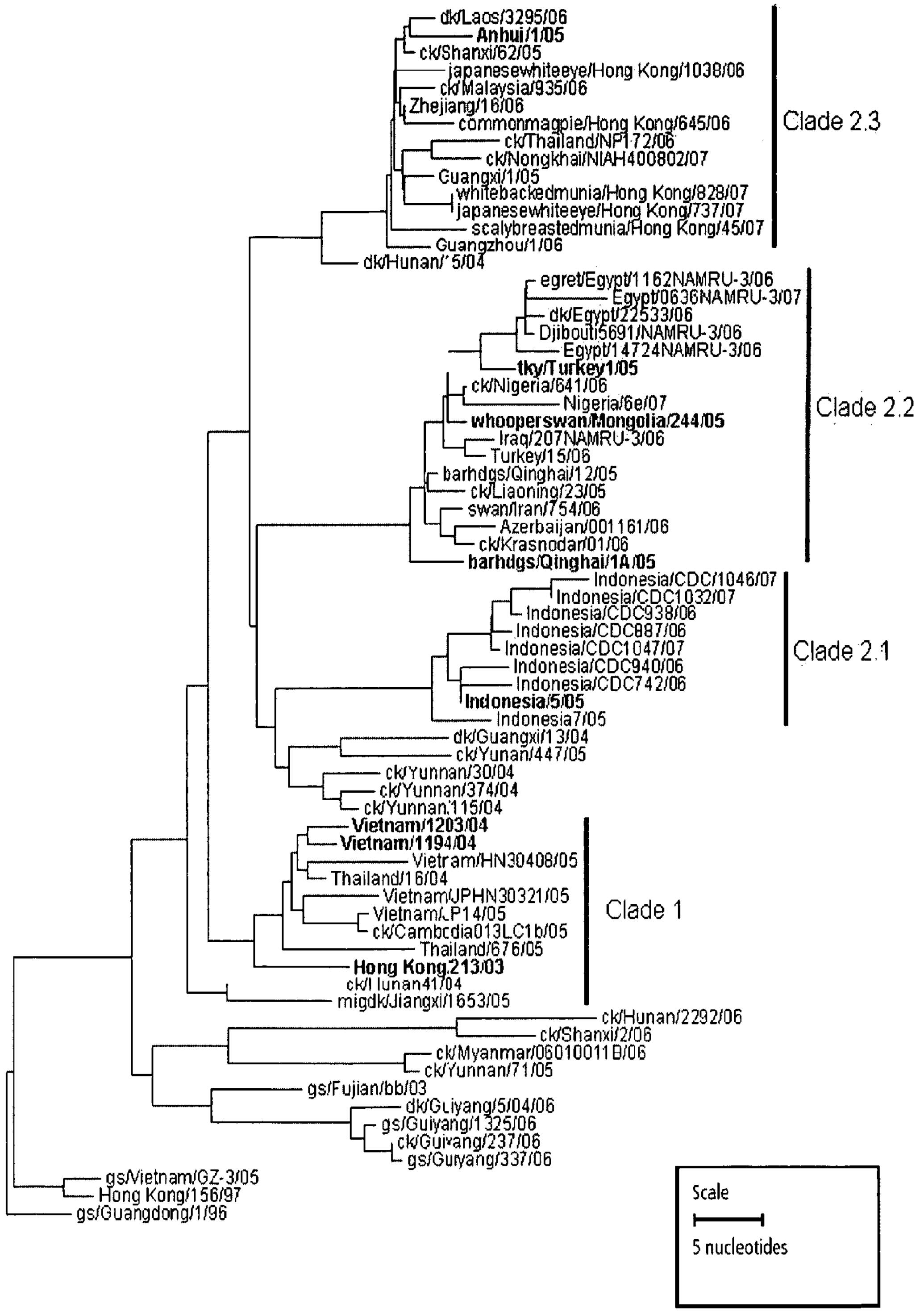
FIGS. 1 and 2 show phylogenetic trees of H5 strains, taken from references 3 and 189.
Figure 2:
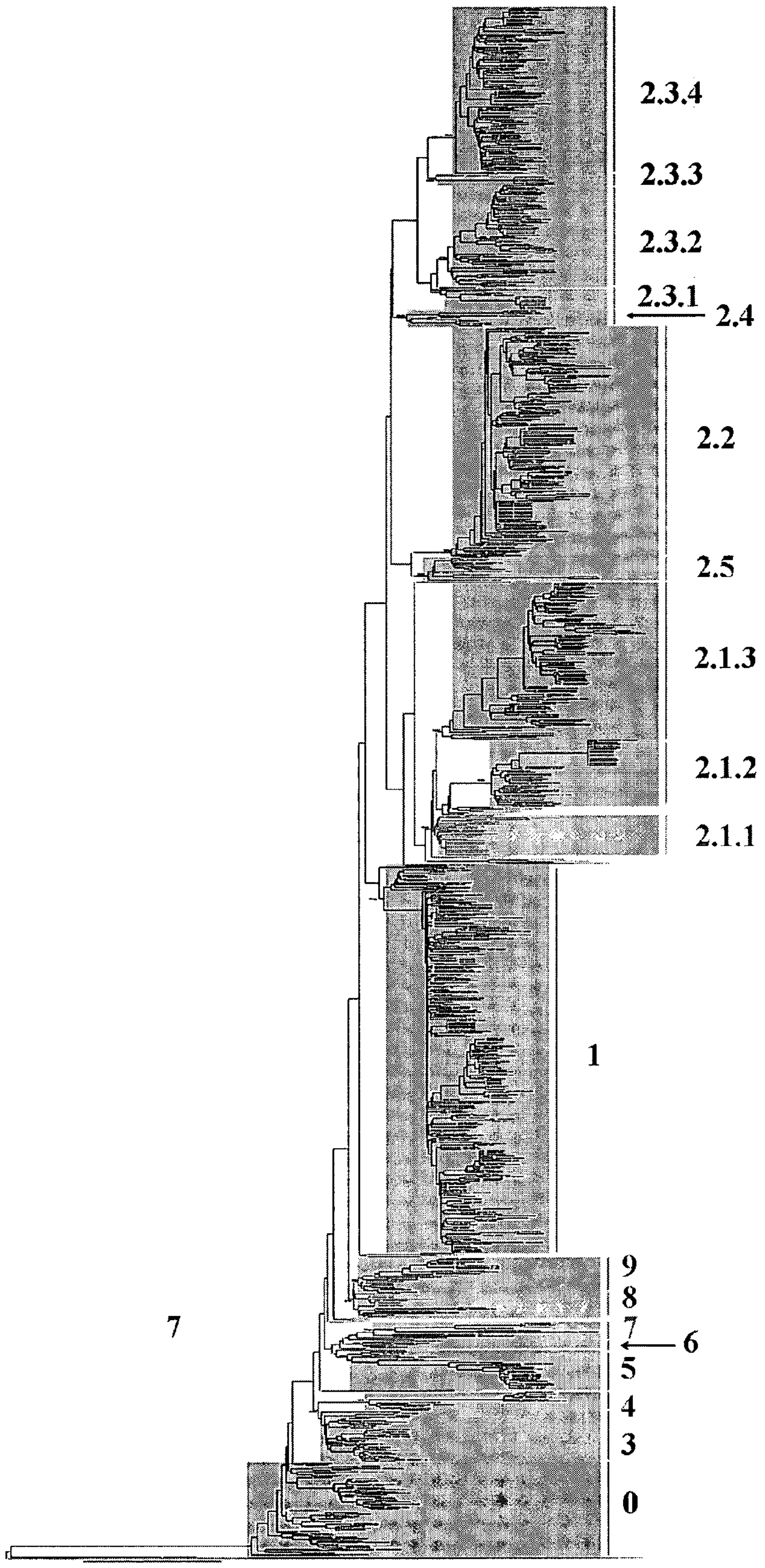

Patients were immunized with an influenza vaccine prepared from H5N3 strain A/duck/Singapore/1997 (clade 0). The vaccine was either unadjuvanted (group 2) or was adjuvanted with the MF59 oil-in-water emulsion (group 1). A third group of patients (group 3) did not receive the H5N3 vaccine.

In a later influenza season (at least 6 years later) patients were immunized with an influenza vaccine prepared from a H5N1 strain (A/Vietnam/1194/2004=clade 1; clade 2 could also be used). Two doses were administered, at days 0 & 21, both containing 7.5 μg of hemagglutinin and MF59 adjuvant. Pre- and post-vaccination antibodies to antigenically diverse H5 viruses were measured by hemagglutination-inhibition (HAI), neutralizing antibody (MN) and single radial hemolysis (SRH).

Results are shown in Table I. In brief, patients who had previously been primed by the clade 0 vaccine mounted a better and more rapid immune response against the new clade than the un-primed patients. Within the primed group, patients who had received an adjuvanted priming dose mounted a better immune response than patients who had received an unadjuvanted priming dose.

Geometric mean antibody titers and sero-responses were significantly higher in primed subjects than in unprimed subjects. By day 7 after one dose of vaccine, ≥80% of patients in group 1 had achieved seroprotective HAI titers of ≥1:40 to all clade 1, 2.1, 2.2, and 2.3 avian H5 virus variants tested, as well as to the original A/duck/Singapore/97 clade 0 antigen. Moreover, there was no evidence to suggest that primed subjects preferentially responded to their original priming antigen, allaying concerns over "original antigenic sin" [190].

Thus it is possible to rapidly induce protective antibody responses against diverse influenza H5N1 viruses following one vaccine dose in subjects primed several years previously with vaccine prepared from a strain in a different H5 clade, antigenically and genetically distant.

Further details of this clinical study are available in reference 191. As noted therein, geometric mean titers of antibodies against a clade 1 strain or a clade 2.2 strain were significantly higher among the primed subjects (groups 1 & 2) than among the unprimed subjects (group 0). From day 14 onwards, titers of antibodies to both viruses were significantly higher in the adjuvant-primed group (group 1) than in the plain-primed group (group 2). The highest titers were observed on day 14 in group 1. No relation between the post-vaccination titer and the number of previous doses of H5N3 vaccine or their antigen content was observed. By day 7, at least 80% of group 1 patients had titers of at least 1:40 for all wildtype viruses tested on hemagglutination-inhibition assay.

Modeling of pandemic spread shows that the maximum reduction in viral transmission is achieved by the induction of a response within 2 weeks after the outbreak of the pandemic. Because two doses of the vaccine would be required, rapid vaccine deployment will thus be difficult. This human study indicates, however, that priming of subjects with H5 antigen (in particular, adjuvanted H5 antigen) induces a rapidly mobilized, long-lasting immune memory after the administration of low-dose, antigenically distinct (different H5 HA clade) vaccine.

In further studies, memory B cells cross-reactive to A/Vietnam/1194/2004 clade 1H5N1 were detected at comparable frequency in the blood of all three patient groups at baseline. Nevertheless, three weeks after the first booster dose, patients in group 1 displayed significantly more H5N1-specific memory B cells than groups 2 and 3, suggesting that earlier priming with adjuvanted H5N3 vaccine had induced a pool of memory B cells with higher cross-reactivity to H5N1. Consistently, patients in group 1, had faster and higher antibody responses than patients in groups 2 or 3, and patients in groups 1 and 2 responded significantly better and faster than patients in group 3. By day 7 after one dose of the clade 1 vaccine, all patients in group 1 had achieved seroconversion to several antigenically distinct highly pathogenic wild-type viruses from clades 0, 1, 2.1.3, 2.2 and 2.3.4, while in group 2 comparable seroconversion rates were observed only by day 14. Conversely, two doses of the clade 1 vaccine were required for group 3 patients to achieve 80% serconversion rates to clade 0 and clade 1 viruses.

Human Study II

Adult and elderly patients received two priming doses (day 0 and day 21) of a H5N1 vaccine adjuvanted with MF59. The virus strain was A/Vietnam/1194/2004, which is classified in clade 1. Immune responses were assessed at day 43 and all three CPMP criteria were satisfied: seroprotection and seroconversion were both at least 80%, and the GMT increase was at least 5-fold.

About 18 months after the two priming doses, up 60 patients are given a further dose of H5N1 vaccine adjuvanted with MF59, but based on strain A/turkey/Turkey/1/05, which is classified in clade 2. Serum samples are collected immediately before this dose, and then both 7 and 21 days later. Immunogenicity is evaluated by HI, SRH, and MN tests on the serum samples.

Human Studies III & IV

Trial NCT00703053 uses a clade 1 vaccine (A/VietNam/1203/04) and/or a clade 2 vaccine (A/Indonesia/05/05). Adults with no previous exposure to H5 strains receive: (a) the clade 1 vaccine at day 0 and the clade 2 vaccine at day 28; (b) the clade 1 vaccine at day 0 and the clade 2 vaccine at day 180; or (c) a combination of the clade 1 and clade 2 vaccines at days 0 and 28. Appropriate controls are also included, receiving only clade 1 vaccine or clade 2 vaccine, but not both. Total antigen dose each time is 90 μg HA, which is either 90 μg from a single strain for groups (a) & (b) or 2×45 μg from each strain for group (c). The study uses unadjuvanted inactivated subvirion vaccines. The study will not be completed until 2010.

Trial NCT00680069 involves administering a single dose of a clade 2 vaccine (A/Indonesia/05/05) to patients who previously received a clade 1 vaccine (A/VietNam/1203/04). The antigen dose is either 15 μg or 90 μg of an inactivated subvirion vaccine. The study will not be completed until 2009.

Mouse Studies I & II (DNA Immunization; for Reference)

In unrelated experiments [192], adenoviral vectors that express HA from A/Vietnam/1203/04 (clade 1) and A/Indonesia/05/05 (clade 2) viruses were constructed.

The vectors were used both separately and in combination to immunize BALB/c mice. The total dose was $10^8$ pfu of vectors, with the combination group receiving $5\times10^7$ pfu of each vector. Four weeks later mice received a booster containing the same vaccine construct(s) and blood was obtained 3 weeks later for detection of neutralizing antibodies and hemagglutination-inhibiting antibodies.

Mice vaccinated with either one of the vectors alone produced hemagglutination-inhibiting and neutralizing antibodies, but no cross-reactivity was detected. However, mice vaccinated with both vectors elicited protective neutralizing antibody titers against viruses from both clades.

In a similar study [193] mice received a combination of either five or ten hemagglutinin DNA immunogens as plasmid expression vectors. A first combination of five HAs was from strains in clades 0, 2.2 (3 strains) and 2.5. A second combination of five HAs was from strains in clades 0, 1, 2.1.3, 2.2 and 2.3.4. The 10-valent was a combination of these 10 strains. The vaccines elicited antibodies that neutralized multiple strains of HPAI H5N1.

Chicken were also tested using 3-valent DNA vaccines of this type [193]. The strains were A/VietNam/1203/04 (clade 1), A/Anhui/1/05 (clade 2.3.4) and A/Indonesia/05/05 (clade 2.1.3). The chicken were protected against disease.

Mouse Study III

As described in detail in reference 8, mice received a bivalent vaccine including H5 hemagglutinin from strains A/VietNam/1203/2004 (clade 1) or A/Indonesia/05/2005 (clade 2). Two types of bivalent vaccine were tested: one based on recombinant H5 hemagglutinin and one based on VLPs. Neither vaccine included an extrinsic adjuvant but, compared to the recombinant proteins, a VLP can provide an intrinsic adjuvant effect due to its particulate nature. Each monovalent VLP was used as a control. Antigens were expressed in Sf9 insect cells from bacmids. Antigens in the bivalent vaccines were mixed at a 1:1 HA weight ratio.

Immune responses were assessed by quantitative ELISA and HAI. All mice vaccinated with the bivalent VLP mixture elicited HAI antibodies against both the VietNam/1203/2004 virus (GMT 115±36) and the Indonesia/05/2005 virus (80±0). In contrast, only 33% of mice vaccinated with a mixture of the unadjuvanted recombinant proteins had an HAI titer against the Indonesia/05/2005 virus (36±12).

Immune responses were also assessed in a lethal challenge study. The challenge strains were PR8/34 reassortants of the two vaccine strains. Unvaccinated mice that were challenged with either virus lost ≥20% of original body weight by day 6 post-infection. Mice vaccinated with the bivalent mixture of recombinant HA proteins lost ~15% of their original body weight when challenged by either the clade 1 or clade 2 challenge strain. Mice vaccinated with the clade 1 VLPs, clade 2 VLPs, or VLP mixture and then challenged with the clade 1 virus had no weight loss and no clinical signs of infection. Mice vaccinated with clade 1 VLPs and then challenged with the clade 2 virus were not protected from challenge, dying by day 6 post-challenge. Mice vaccinated with clade 2 VLPs or the VLP mixture were all protected from clade 2 virus challenge.

Thus the clade 1 and clade 2 VLPs were both immunogenic in mice and protected against virus challenge with the homologous strain. The immunogenicity was retained if a bivalent mixture of the VLPs was used. Moreover, mice who had received the bivalent VLPs were protected against challenge by either the clade 1 or clade 2 virus. As reported in reference 8: "These results are highly significant and demonstrate that a multivalent vaccine against H5N1 appears to be a plausible strategy to combat the diversity of clades and subclades of H5N1 influenza."

It will be understood that the invention has been described by way of example only and modifications may be made whilst remaining within the scope and spirit of the invention.

TABLE I

| Measure | G 1 | G 2 | G 3 |
|---|---|---|---|
| % of patients with HI titer ≥40 at day 0 | 0 | 0 | 3 |
| at day 8 | 75 | 56 | 12 |
| at day 15 | 90 | 60 | 9 |
| at day 22 | 75 | 58 | 13 |
| at day 43 | 75 | 58 | 45 |
| % of patients with seroconversion at day 8 | 75 | 56 | 8 |
| at day 15 | 90 | 60 | 10 |
| at day 22 | 75 | 58 | 14 |
| at day 43 | 75 | 58 | 45 |

TABLE I-continued

| Measure | G 1 | G 2 | G 3 |
|---|---|---|---|
| Geometric mean HI at day 1 | 4 | 4 | 4.9 |
| day 8 | 72 | 51 | 5.9 |
| day 15 | 256 | 79 | 7.3 |
| day 22 | 112 | 52 | 8.0 |
| day 43 | 95 | 44 | 26 |
| Ratio of HI relative to day 1 at day 8 | 18 | 13 | 1.3 |
| at day 15 | 64 | 20 | 1.56 |
| at day 22 | 28 | 13 | 1.8 |
| at day 43 | 24 | 11 | 5.9 |
| % of patients with MN titer ≥80 at day 0 | 0 | 0 | 0 |
| at day 8 | 9 | 5 | 1 |
| at day 15 | 9 | 9 | 1 |
| at day 22 | 12 | 9 | 1 |
| at day 43 | 12 | 10 | 5 |
| Geometric mean MN titer at day 1 | 10 | 10 | 10 |
| day 8 | 219 | 151 | 11 |
| day 15 | 1145 | 473 | 12 |
| day 22 | 375 | 324 | 12 |
| day 43 | 415 | 241 | 33 |
| Ratio of MN relative to day 1 at day 8 | 22 | 15 | 1.1 |
| at day 15 | 115 | 47 | 1.2 |
| at day 22 | 37 | 32 | 1.2 |
| at day 43 | 41 | 24 | 3.3 |

REFERENCES

[1] Riley et al. (2007) *PLoS Med.* 4(6):e218.
[2] Felsenstein (1989) *Cladistics* 5: 164-166.
[3] *Emerging Infectious Diseases* 11(10):1515-21.
[4] WO96/37624.
[5] WO98/46262.
[6] WO95/18861.
[7] Bright et al. (2008) *PLoS ONE* 3:e1501.
[8] Crevar & Ross (2008) *Virology Journal* 5:131.
[9] WO02/28422.
[10] WO02/067983.
[11] WO02/074336.
[12] WO01/21151.
[13] WO02/097072.
[14] WO2005/113756.
[15] Huckriede et al. (2003) *Methods Enzymol* 373:74-91.
[16] WO2005/107797.
[17] Herlocher et al. (2004) *J Infect Dis* 190(9):1627-30.
[18] Hoffmann et al. (2002) *Vaccine* 20:3165-3170.
[19] Subbarao et al. (2003) *Virology* 305:192-200.
[20] Liu et al. (2003) *Virology* 314:580-590.
[21] Ozaki et al. (2004) *J. Virol.* 78:1851-1857.
[22] Webby et al. (2004) *Lancet* 363:1099-1103.
[23] WO00/60050.
[24] WO01/04333.
[25] U.S. Pat. No. 6,649,372.
[26] WO2007/002008.
[27] Neumann et al. (2005) *Proc Natl Acad Sci USA* 102:16825-9.
[28] WO2006/067211.
[29] WO01/83794.
[30] Hoffmann et al. (2000) *Virology* 267(2):310-7.
[31] WO97/37000.
[32] Brands et al. (1999) *Dev Biol Stand* 98:93-100.
[33] Halperin et al. (2002) *Vaccine* 20:1240-7.
[34] Tree et al. (2001) *Vaccine* 19:3444-50.
[35] Kistner et al. (1998) *Vaccine* 16:960-8.
[36] Kistner et al. (1999) *Dev Biol Stand* 98:101-110.
[37] Bruhl et al. (2000) *Vaccine* 19:1149-58.
[38] Pau et al. (2001) *Vaccine* 19:2716-21.
[39] WO03/076601.

[40] WO2005/042728.
[41] WO03/043415.
[42] WO01/85938.
[43] WO2006/108846.
[44] EP-A-1260581 (WO01/64846).
[45] WO2006/071563.
[46] WO2005/113758.
[47] WO2006/027698.
[48] WO97/37000
[49] WO03/023021
[50] WO03/023025
[51] WO97/37001.
[52] WO01/22992.
[53] Hehme et al. (2004) *Virus Res.* 103(1-2):163-71.
[54] Treanor et al. (1996) *J Infect Dis* 173:1467-70.
[55] Keitel et al. (1996) *Clin Diagn Lab Immunol* 3:507-10.
[56] Zangwill et al. (2008) *J Infect Dis.* 197(4):580-3.
[57] Lundblad (2001) *Biotechnology and Applied Biochemistry* 34:195-197.
[58] *Guidance for Industry: Bioanalytical Method Validation*. U.S. Department of Health and Human Services Food and Drug Administration Center for Drug Evaluation and Research (CDER) Center for Veterinary Medicine (CVM). May 2001.
[59] Ji et al. (2002) *Biotechniques.* 32:1162-7.
[60] Briggs (1991) *J Parenter Sci Technol.* 45:7-12.
[61] Lahijani et al. (1998) *Hum Gene Ther.* 9:1173-80.
[62] Lokteff et al. (2001) *Biologicals.* 29:123-32.
[63] EP-B-0870508.
[64] U.S. Pat. No. 5,948,410.
[65] WO2007/052163.
[66] U.S. Pat. No. 6,355,271.
[67] WO00/23105.
[68] U.S. Pat. No. 4,680,338.
[69] U.S. Pat. No. 4,988,815.
[70] WO92/15582.
[71] Stanley (2002) *Clin Exp Dermatol* 27:571-577.
[72] Wu et al. (2004) *Antiviral Res.* 64(2):79-83.
[73] Vasilakos et al. (2000) *Cell Immunol.* 204(1):64-74.
[74] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[75] Jones (2003) *Curr Opin Investig Drugs* 4:214-218.
[76] WO2004/060308.
[77] U.S. Pat. No. 6,924,271.
[78] US2005/0070556.
[79] U.S. Pat. No. 5,658,731.
[80] WO2004/064759.
[81] U.S. Pat. No. 5,011,828.
[82] WO2004/87153.
[83] U.S. Pat. No. 6,605,617.
[84] WO02/18383.
[85] WO2004/018455.
[86] WO03/082272.
[87] WO2006/002422.
[88] Johnson et al. (1999) *Bioorg Med Chem Lett* 9:2273-2278.
[89] Evans et al. (2003) *Expert Rev Vaccines* 2:219-229.
[90] Andrianov et al. (1998) *Biomaterials* 19:109-115.
[91] Payne et al. (1998) *Adv Drug Delivery Review* 31:185-196.
[92] U.S. Pat. No. 5,057,540.
[93] WO96/33739.
[94] EP-A-0109942.
[95] WO96/11711.
[96] WO00/07621.
[97] Barr et al. (1998) *Advanced Drug Delivery Reviews* 32:247-271.
[98] Sjolanderet et al. (1998) *Advanced Drug Delivery Reviews* 32:321-338.
[99] Pizza et al. (2000) *Int J Med Microbiol* 290:455-461.
[100] WO95/17211.
[101] WO98/42375.
[102] Singh et al] (2001) *J Cont Release* 70:267-276.
[103] WO99/27960.
[104] U.S. Pat. No. 6,090,406
[105] U.S. Pat. No. 5,916,588
[106] EP-A-0626169.
[107] WO99/52549.
[108] WO01/21207.
[109] WO01/21152.
[110] WO02/072012.
[111] Dyakonova et al. (2004) Int Immunopharmacol 4(13):1615-23.
[112] FR-2859633.
[113] Signorelli & Hadden (2003) *Int Immunopharmacol* 3(8):1177-86.
[114] WO2004/064715.
[115] De Libero et al, *Nature Reviews Immunology,* 2005, 5:485-496.
[116] U.S. Pat. No. 5,936,076.
[117] Oki et al, *J. Clin. Investig.,* 113: 1631-1640
[118] US2005/0192248
[119] Yang et al, *Angew. Chem. Int. Ed.,* 2004, 43: 3818-3822
[120] WO2005/102049
[121] Goff et al, *J. Am. Chem., Soc.,* 2004, 126: 13602-13603
[122] WO03/105769
[123] Cooper (1995) *Pharm Biotechnol* 6:559-80.
[124] WO03/011223.
[125] Meraldi et al. (2003) *Vaccine* 21:2485-2491.
[126] Pajak et al. (2003) *Vaccine* 21:836-842.
[127] U.S. Pat. No. 6,586,409.
[128] Wong et al. (2003) *J Clin Pharmacol* 43(7):735-42.
[129] US2005/0215517.
[130] WO90/14837.
[131] Podda & Del Giudice (2003) *Expert Rev Vaccines* 2:197-203.
[132] Podda (2001) *Vaccine* 19: 2673-2680.
[133*] Vaccine Design: The Subunit and Adjuvant Approach* (eds. Powell & Newman) Plenum Press 1995 (ISBN 0-306-44867-X).
[134] *Vaccine Adjuvants: Preparation Methods and Research Protocols* (Volume 42 of *Methods in Molecular Medicine* series). ISBN: 1-59259-083-7. Ed. O'Hagan.
[135] Allison & Byars (1992) *Res Immunol* 143:519-25.
[136] Hariharan et al. (1995) *Cancer Res* 55:3486-9.
[137] US-2007/014805.
[138] WO95/11700.
[139] U.S. Pat. No. 6,080,725.
[140] WO2005/097181.
[141] WO2006/113373.
[142] Han et al. (2005) *Impact of Vitamin E on Immune Function and Infectious Diseases in the Aged at Nutrition, Immune functions and Health* EuroConference, Paris, 9-10 Jun. 2005.
[143] U.S. Pat. No. 6,630,161.
[144] Kandimalla et al. (2003) *Nucleic Acids Research* 31:2393-2400.

[145] WO02/26757.
[146] WO99/62923.
[147] Krieg (2003) *Nature Medicine* 9:831-835.
[148] McCluskie et al. (2002) *FEMS Immunology and Medical Microbiology* 32:179-185.
[149] WO98/40100.
[150] U.S. Pat. No. 6,207,646.
[151] U.S. Pat. No. 6,239,116.
[152] U.S. Pat. No. 6,429,199.
[153] Kandimalla et al. (2003) *Biochemical Society Transactions* 31 (part 3):654-658.
[154] Blackwell et al. (2003) *J Immunol* 170:4061-4068.
[155] Krieg (2002) *Trends Immunol* 23:64-65.
[156] WO01/95935.
[157] Kandimalla et al. (2003) *BBRC* 306:948-953.
[158] Bhagat et al. (2003) *BBRC* 300:853-861.
[159] WO03/035836.
[160] WO01/22972.
[161] Schellack et al. (2006) *Vaccine* 24:5461-72.
[162] Thompson et al. (2005) *J Leukoc Biol* 78:1273-80.
[163] UK patent application GB-A-2220211.
[164] WO 94/21292.
[165] WO94/00153.
[166] WO95/17210.
[167] WO96/26741.
[168] WO93/19780.
[169] Gennaro (2000) *Remington: The Science and Practice of Pharmacy*. 20th edition, ISBN: 0683306472.
[170] Banzhoff (2000) *Immunology Letters* 71:91-96.
[171] Nony et al. (2001) *Vaccine* 27:3645-51.
[172] WO2005/089837.
[173] U.S. Pat. No. 6,692,468.
[174] WO00/07647.
[175] WO99/17820.
[176] U.S. Pat. No. 5,971,953.
[177] U.S. Pat. No. 4,060,082.
[178] EP-A-0520618.
[179] WO98/01174.
[180] Potter & Oxford (1979) *Br Med Bull* 35: 69-75.
[181] Greenbaum et al. (2004) *Vaccine* 22:2566-77.
[182] Zurbriggen et al. (2003) *Expert Rev Vaccines* 2:295-304.
[183] Piascik (2003) *J Am Pharm Assoc* (*Wash DC*). 43:728-30.
[184] Mann et al. (2004) *Vaccine* 22:2425-9.
[185] Halperin et al. (1979) *Am J Public Health* 69:1247-50.
[186] Herbert et al. (1979) *J Infect Dis* 140:234-8.
[187] Chen et al. (2003) *Vaccine* 21:2830-6.
[188] WO2008/115785.
[189] *Towards a unified nomenclature system for the highly pathogenic H5N1 avian influenza viruses*. WHO/OIE/FAO H5N1 evolution working group.
[190] Haaheim (2003) *Dev Biol* 115: 49-53.
[191] Stephenson et al. (2008) *N Engl J Med* 359:1631-33.
[192] Hoelscher et al. (2008) *J Infect Dis* 197:1185-8.
[193] Rao et al. (2008) *PLoS ONE* 3(6):e2432.

The invention claimed is:

1. A method for immunizing a patient, the method comprising a step of: administering to the patient an immunogenic composition comprising a hemagglutinin antigen from a second clade of H5 influenza A virus, wherein the patient was previously immunized with an adjuvanted influenza vaccine comprising a hemagglutinin antigen from a first clade of H5 influenza A virus;

wherein the adjuvanted influenza vaccine comprises an oil-in-water emulsion;

and wherein the first and the second clades are different.

2. The method of claim 1, wherein the immunogenic composition comprises 15 μg, 7.5 μg, or 3.75 μg hemagglutinin antigen from the second clade of H5 influenza A virus.

3. The method of claim 1, wherein the patient was immunized with the adjuvanted influenza vaccine comprising the hemagglutinin antigen from the first clade of H5 influenza A virus at least 9 months, at least 12 months, at least 18 months, at least 24 months, at least 36 months, at least 48 months or at least 60 months previously.

4. The method of claim 1, where the first clade is clade 1 and the second clade is clade 2.

5. The method of claim 1, where the first clade is clade 2 and the second clade is clade 1.

6. The method of claim 1, where the first clade is clade 1 and the second clade is not clade 2.

7. The method of claim 1, where the first clade is clade 2 and the second clade is not clade 1.

8. The method of claim 1, wherein the immunogenic composition and/or the adjuvanted influenza vaccine is a split vaccine.

9. The method of claim 1, wherein the immunogenic composition and/or the adjuvanted influenza vaccine is a purified subunit vaccine.

10. The method of claim 1, wherein the immunogenic composition and/or the adjuvanted influenza vaccine includes influenza A virus neuraminidase.

11. The method of claim 1, wherein the immunogenic composition comprising the second clade antigen is adjuvanted with an oil-in-water emulsion-adjuvant.

12. A method for immunizing a patient, the method comprising steps of:

(i) administering to the patient a first influenza vaccine comprising a hemagglutinin antigen from a first clade of H5 influenza A virus and an oil-in-water emulsion; and (ii) administering to the patient a second influenza vaccine comprising a hemagglutinin antigen from a second clade of H5 influenza A virus;

wherein the first and the second clades are different.

13. The method of claim 12, wherein the influenza vaccine comprises 15 μg, 7.5 μg, or 3.75 μg hemagglutinin antigen from the second clade of H5 influenza A virus.

14. The method of claim 12, wherein the influenza vaccine comprising the hemagglutinin antigen from the first clade of H5 influenza A virus is administered at least 9 months, at least 12 months, at least 18 months, at least 24 months, at least 36 months, at least 48 months or at least 60 months before administration of the influenza vaccine comprising the hemagglutinin antigen from the second clade of H5 influenza A virus.

15. The method of claim 12, where the first clade is clade 1 and the second clade is clade 2.

16. The method of claim 12, where the first clade is clade 2 and the second clade is clade 1.

17. The method of claim 12, where the first clade is clade 1 and the second clade is not clade 2.

18. The method of claim 12, where the first clade is clade 2 and the second clade is not clade 1.

19. The method of claim 12, wherein the first and/or the second influenza vaccine is a split vaccine.

20. The method of claim 12, wherein the first and/or the second influenza vaccine is a purified subunit vaccine.

21. The method of claim 12, wherein the first and/or the second influenza vaccine includes influenza A virus neuraminidase.

22. The method of claim 12, wherein the influenza vaccine comprising the second clade antigen is adjuvanted with an oil-in-water emulsion adjuvant.

23. The method of claim 1, wherein the immunogenic composition comprises <15μg hemagglutinin antigen from the second clade of H5 influenza A virus.

24. The method of claim 12, wherein the influenza vaccine comprises <15μg hemagglutinin antigen from the second clade of H5 influenza A virus.

* * * * *

SEQUENCE LISTING

<160> NUMBER OF SEQ ID NOS: 16

<210> SEQ ID NO 1
<211> LENGTH: 1707
<212> TYPE: DNA
<213> ORGANISM: Influenza A virus (A/Hong Kong/213/03)

<400> SEQUENCE: 1
atggagaaaa tagtgcttct tttgcaata gtcagtcttg ttaaaagtga tcagatttgc 60
attggttacc atgcaaacaa ctcgacagag caggttgaca caataatgga aaagaacgtt 120
actgttacac atgcccaaga catactggaa aagacacaca acgggaagct ctgcgatcta 180
gatggagtga agcctctaat tttgagagat tgtagtgtag ctggatggct cctcggaaac 240
ccaatgtgtg acgaattcat caatgtgccg gaatggtctt acatagtgga gaaggccaat 300
ccagccaatg acctctgtta cccaggggat ttcaacgact atgaagaatt gaaacaccta 360
ttgagcagaa taaaccattt tgagaaaatt cagatcatcc ccaaaaattc ttggtccagt 420
catgaagcct cattaggggt gagctcagca tgtccatacc aaggaaagtc ctcctttttc 480
aggaatgtgg tatggcttat caaaaagaac aatgcatacc caacaataaa gaggagctac 540
aataatacca accaagaaga tcttttggta ttgtggggga ttcaccatcc taatgatgcg 600
gcagagcaga ctaggctcta tcaaaaccca accacctaca tttccgttgg gacatcaaca 660
ctaaaccaga gattggtacc aaaaatagct actagatcca aagtaaacgg gcaaaatgga 720
aggatggagt tcttctggac aattttaaaa ccgaatgatg caatcaactt cgagagcaat 780
ggaaatttca ttgctccaga atatgcatac aaaattgtca agaaagggga ctcagcaatt 840
atgaaaagtg aattggaata tggtaactgc aacaccaagt gtcaaactcc aatgggggcg 900
ataaactcta gtatgccatt ccacaatata caccctctca ccatcgggga atgccccaaa 960
tatgtgaaat caaacagatt agtccttgcg actgggctca gaaatagccc tcaaagagag 1020

```
agaagaagaa aaaagagagg attatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactcg   1200

atcattgaca aaatgaacac tcagtttgag gccgttggaa gggaatttaa taacttagaa   1260

aggagaatag agaatttaaa caagaagatg gaagacggat tcctagatgt ctggacttat   1320

aatgctgaac ttctggttct catggaaaat gagagaactc tagactttca tgactcaaat   1380

gtcaagaacc tttacgacaa ggtccgacta cagcttaggg ataatgcaaa ggagctgggt   1440

aacggttgtt tcgagttcta tcacaaatgt gataatgaat gtatggaaag tgtaagaaac   1500

ggaacgtatg actacccgca gtattcagaa gaagcaagac taaaaagaga ggaaataagt   1560

ggagtaaaat tggagtcaat aggaacttac caaatactgt caatttattc tacagtggcg   1620

agttccctag cactggcaat catggtagct ggtctatctt tatggatgtg ctccaatggg   1680

tcgttacaat gcagaatttg catttaa                                     1707


<210> SEQ ID NO 2
<211> LENGTH: 1707
<212> TYPE: DNA
<213> ORGANISM: Influenza A virus (A/Indonesia/5/05)

<400> SEQUENCE: 2

atggagaaaa tagtgcttct tcttgcaata gtcagtcttg ttaaaagtga tcagatttgc     60

attggttacc atgcaaacaa ttcaacagag caggttgaca caatcatgga aaagaacgtt    120

actgttacac atgcccaaga catactggaa aagacacaca acgggaagct ctgcgatcta    180

gatggagtga agcctctaat tttaagagat tgtagtgtag ctggatggct cctcgggaac    240

ccaatgtgtg acgaattcat caatgtaccg gaatggtctt acatagtgga gaaggccaat    300

ccaaccaatg acctctgtta cccagggagt ttcaacgact atgaagaact gaaacaccta    360

ttgagcagaa taaaccattt tgagaaaatt caaatcatcc ccaaaagttc ttggtccgat    420

catgaagcct catcaggagt gagctcagca tgtccatacc tgggaagtcc ctcctttttt    480

agaaatgtgg tatggcttat caaaaagaac agtacatacc caacaataaa gaaaagctac    540

aataatacca accaagaaga tcttttggta ctgtggggaa ttcaccatcc taatgatgcg    600

gcagagcaga caaggctata tcaaaaccca accacctata tttccattgg gacatcaaca    660

ctaaaccaga gattggtacc aaaaatagct actagatcca aagtaaacgg gcaaagtgga    720

aggatggagt tcttctggac aattttaaaa cctaatgatg caatcaactt cgagagtaat    780

ggaaatttca ttgctccaga atatgcatac aaaattgtca agaaagggga ctcagcaatt    840

atgaaaagtg aattggaata tggtaactgc aacaccaagt gtcaaactcc aatgggggcg    900

ataaactcta gtatgccatt ccacaacata caccctctca ccatcgggga atgccccaaa    960

tatgtgaaat caaacagatt agtccttgca acagggctca gaaatagccc tcaaagagag   1020

agcagaagaa aaaagagagg actatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactca   1200

atcattgaca aaatgaacac tcagtttgag gccgttggaa gggaatttaa taacttagaa   1260

aggagaatag agaatttaaa caagaagatg gaagacgggt ttctagatgt ctggacttat   1320

aatgccgaac ttctggttct catggaaaat gagagaactc tagactttca tgactcaaat   1380
```

gttaagaacc tctacgacaa ggtccgacta cagcttaggg ataatgcaaa ggagctgggt 1440
aacggttgtt tcgagttcta tcacaaatgt gataatgaat gtatggaaag tataagaaac 1500
ggaacgtaca actatccgca gtattcagaa gaagcaagat taaaaagaga ggaaataagt 1560
ggggtaaaat tggaatcaat aggaacttac caaatactgt caatttattc aacagtggcg 1620
agttccctag cactggcaat catgatggct ggtctatctt tatggatgtg ctccaatgga 1680
tcgttacaat gcagaatttg catttaa 1707

<210> SEQ ID NO 3
<211> LENGTH: 1654
<212> TYPE: DNA
<213> ORGANISM: Influenza A virus (A/Chicken/Hong Kong/SF219/01)

<400> SEQUENCE: 3
agtcttgtta aaagtgatca gatttgcatt ggttaccatg caaacaactc gacagagcag 60
gttgacacaa taatggaaaa gaacgttact gttacacatg cccaagacat attggaaaag 120
acacacaatg ggaagctctg cgatctagat ggagtgaagc ctctaatttt gagagattgt 180
agtgtagctg gatggctcct cggaaaccca atgtgtgacg aattcatcaa tgtgccggaa 240
tggtcttaca tagtggagaa ggccagtcca gccaatgacc tctgttaccc aggggatttc 300
aacgactatg aagaactgaa acacctattg agcagaataa accattttga gaaaattcag 360
atcatcccca aaagttcttg gtccaatcat gaagcctcat caggggtgag ctcagcatgt 420
ccataccttg ggaagtcctc ctttttcaga aatgtggtat ggcttatcaa aaagaacagt 480
acatacccaa caataaagag gagctataat aataccaacc aagaagatct tttggtactg 540
tgggggattc accatcctaa tgatgcggca gagcagacaa agctctatca aaacccaacc 600
acctatattt ccgttggaac atcaacacta aaccagagat tggtaccaaa aatagctact 660
agatccaaag taaacgggca aagtggaaga atggagttct tctggacaat tttaaagccg 720
aatgatgcta tcaatttcga gagtaatgga aatttcattg ctccagaata tgcatacaaa 780
attgtcaaga aaggggactc atcaattatg aaaagtgaat tggaatatgg taactgcaac 840
accaagtggc aaactccaat gggggcgata aactctagta tgccattcca caacatacac 900
cctctcacca tcggggaatg ccccaaatat gtgaaatcaa acagattagt ccttgcgact 960
ggactcagaa ataccccctca aagagagaga agaagaaaaa agagaggact atttggagct 1020
atagcaggtt ttatagaggg aggatggcag ggaatggtag atggttggta tgggtaccac 1080
catagcaatg agcaggggag tggatacgct gcagacaaag aatccactca aaaggcaata 1140
gatggagtta ccaataaggt caactcgatc attgacaaaa tgaacactca gtttgaggcc 1200
gttggaaggg aatttaataa cttagaaagg agaatagaaa atttaaacaa gaagatggaa 1260
gacggattcc tagatgtctg gacttataat gctgaacttc tggttctcat ggaaaatgag 1320
agaactctag actttcacga ctcaaatgtc aagaaccttt acgacaaggt ccgactacag 1380
cttagggata atgcaaagga gctgggtaac ggctgtttcg agttctatca caaatgtgat 1440
aatgaatgta tggaaagtgt aaaaaacgga acgtatgact acccgcagta ttcagaagaa 1500
gcaagactaa acagagagga aataagtgga gtaaaattgg aatcaatggg aacttaccaa 1560
atactgtcaa tttattcaac agtggcgagt tccctagcac tggcaatcat ggtagctggt 1620
ctatctttat ggatgtgctc caatggatcg ttac 1654

<210> SEQ ID NO 4
<211> LENGTH: 1668

-continued

<212> TYPE: DNA
<213> ORGANISM: Influenza A virus (A/chicken/Guiyang/441/2006)

<400> SEQUENCE: 4

```
atggagaaaa tagtgcttct tcttgcaata atcagtcttg ttaaaagtga tcagatttgc      60

attggttacc atgcaaacaa ctcgacagtg caggttgaca cgataatgga aaagaatgtt     120

actgtaacac atgcccaaga catactggaa aagacacaca atgggaagct ctgcagtcta     180

gatggagtga agcctctaat tttaagagat tgtagtgtag ctggatggct cctcggaaac     240

ccaatgtgtg acgaattcat caatgtgccc gaatggtctt acatagtgga gaaggccagt     300

ccagccaatg acctctgtta cccaggggat ttcaacgact acgaagaact gaaacaccta     360

ttgagcagaa taaaccattt tgagaaaatt cagatcatcc ccaaaagttc ttggcccaat     420

catgaagcct cactaggggt gagctcagca tgtccatacc tgggggagtc ctcctttttc     480

agaaatgtgg tatggcttat caaaaagaac agttcatacc caacaataaa gaggagctac     540

aataatacca accaagaaga tcttttagta ttgtggggga tccatcaccc taatgatgcg     600

gcagagcaga taaagcttta tcaaaaccca aacacctata tttccgttgg aacatcaaca     660

ctaaaccaga ggttggtacc aacaatagct actagatcca aagtaaacgg gcaaagtgga     720

aggatggagt tcttctggac aattttaaag ccgaatgata ctatcaattt cgagagtaat     780

ggaaatttca ttgctccaga atatgcatac aaaattgtca agaaagggga ctcagcaatt     840

atgaaaagtg aattggaata tggtaactgc aacaccaagt gtcaaactcc aatgggggcg     900

ataaactcta gtatgccatt ccacaacata caccctctca ccatcgggga atgccccaaa     960

tatgtgaaat caaacagatt agtccttgca actggactca gaaataccct tcaaagagag    1020

agaaggagaa aaaagagagg actatttgga gccatagcag gttttattga gggaggatgg    1080

cagggaatgg tagacggttg gtatgggtac caccatagca atgagcaggg gagtggatac    1140

gctgcagaca aagaatccac tcaaaaggca atagatggaa tcaccaataa ggtcaactcg    1200

atcattaaca aaatgaacac tcagtttgag gccgttggac gggaatttag taacttagaa    1260

aggagaatag aaaatttaaa caagaagatg gaagacggat tcctagatgt ctggacttat    1320

aatgctgaac ttctggttct catggaaaat gaaagaactc tagactttca tgactcaaat    1380

gtcaagaacc tttacgacaa agtccgacta cagcttaggg ataatgcaaa agagctgggt    1440

aacggttgtt tcgagttcta tcacaaatgt gatgatgaat gtatggaaag tgtaaaaaac    1500

ggaacgtatg actacccgca gtattcagaa gaagctagac taaacagaga ggagataaat    1560

ggagtaaaat tggaatcaat gggaacctac caaatactgt caatttactc aacagtggcg    1620

agttccctag cactggcaat catggtagct ggtctatctt tatggatg                 1668
```

<210> SEQ ID NO 5
<211> LENGTH: 1698
<212> TYPE: DNA
<213> ORGANISM: Influenza A virus (A/duck/Guangxi/1681/2004)

<400> SEQUENCE: 5

```
atggagaaaa tagtgcttct tcttgcaata gtcagtcttg ttaaaagtga tcagatttgc      60

attggttacc atgcaaacaa ctcgacagag caggttgata caataatgga aaagaatgtt     120

actgttacac atgcccaaga catactggaa aagacacaca acgggaaact ctgcgatcta     180

gatggagtga agcctctaat tttgagagat tgtagtgttg cgggatggct cctcggaaac     240

ccaatgtgtg atgaattcat caatgtgccg gaatggtctt acatagtgga gaaggccagt     300
```

-continued

```
ccagccaatg acctctgtta cccaggagat ttcaacgact atgaagaact aaaacaccta    360

ttgagcagaa taaatcattt tgagaaaatt cagatcatcc ccaaaagttc ttggtccaat    420

catgaagcct catcaggggt gagctcagca tgtccatacc aggggaggcc ctcctttttc    480

aggaatgtgg tatggcttat caaaaagaac agtgcatacc ctacaataaa gaggagctac    540

aataatacca gtcaagaaga tcttttggta ctgtgggga ttcaccatcc taatgatgcg    600

gcagagcaga caaagctcta tcaaaaccca actacctata tttccgttgg aacatcaaca    660

ctaaaccaga gattggtacc aaaaatagct actagatcca aagtaaacgg gcagagtgga    720

agaatggagt tcttctggac aattttaaag ccgaatgatg ctatcaactt cgagagtaat    780

ggaaatttca ttgctccaga atatgcctac aaaattgtca agaaagggga ctcagcaatt    840

atgaaaagtg aattggaata tggtaactgc aacaccaaat gtcaaactcc aatgggggcg    900

ataaactcta gtatgccatt ccacaacata caccctctca ccatcgggga atgccccaag    960

tatgtgaaat caagcagatt agtccttgcg acagggctca ggaatagccc tcaaagagag   1020

ataagaagaa aaaagagagg actatttgga gctatagcag gctttataga gggaggatgg   1080

cagggaatgg tagatggttg gtatgggtac caccatagca acgagcaggg gagtggatac   1140

gctgcagaca aagaatccac tcaaaaggca atagatggag tcaccaataa agtcaattcg   1200

atcattgaca aaatgaacac tcaatttgag gccgttggaa gggaatttaa taatttagaa   1260

aggagaatag agaatttaaa caaaaagatg gaggacggat tcctagatgt ctggacttat   1320

aatgctgaac ttctggttct catggaaaat gagagaactc tagactttca tgactcaaat   1380

gtcaagaacc tttacgacag ggtccgacta cagcttaggg ataatgcaaa ggagctgggg   1440

aacggttgtt tcgagttcta tcacaagtgt gacaatgaat gcatggaaag tgtaagaaac   1500

ggaacgtatg actacccgca gtattcagaa gaagcaagac taaagagaga ggaaataagt   1560

ggagtaaaat tggaatcgat aggaacttac caaatattgt caatttattc aacagtggcg   1620

agttccctag cactggcaat catggtagct ggtctatctt tatggatgtg ctccaatgga   1680

tcgttacaat gcagaatt                                                 1698


<210> SEQ ID NO 6
<211> LENGTH: 1707
<212> TYPE: DNA
<213> ORGANISM: Influenza A virus (A/tree sparrow/Henan/4/2004)

<400> SEQUENCE: 6

atggagaaaa tagtgcttct tcttgcaata gtcagtcttg ttaaaagtga tcagatttgc     60

attggttacc atgcaaacaa ctcgacagag caggttgaca caataatgca aaagaacgtt    120

actgttacac atgcccaaga catactggaa aagacacaca acgggaagct ctgcgatcta    180

gatggagtga aacctctaat tttaagagat tgtagtgtag ctggatggct cctcggaaac    240

ccaatgtgtg acgaattcat caatgtgccg gaatggtctt acatagtgga gaaggccagt    300

ccagccaatg acctctgtta cccaggggat ttcaacgact atgaagaact gaaacaccta    360

ttgagcagaa taaaccattt tgagaaaatt cagatcatcc ccaaaagttc ttggtccgat    420

catgaagcct catcaggggt gagctcagca tgtccatacc aggggagtcc ctcctttttc    480

agaaatgtgg tatggcttat caaaaagaac agtgcatacc caacaataaa gaggagctac    540

aataatacca accaagaaga tcttttggta ctgtgggga ttcaccatcc taatgatgcg    600

gcagagcaga caaagctcta tcaaaaccca accacctata tttccgttgg aacatcaaca    660

ctaaaccaga gattggtacc aaaaatagct actagatcca aagtaaatgg gcaaagtgga    720
```

-continued

```
agaatggagt tcttctggac aattttaaag ccgaatgacg ctatcaactt cgagagtaat    780
ggaaatttca ttgctccaga atatgcatac aaaattgtca agaaagggga ctcagcaatt    840
atgaaaagtg aattggaata tggtaactgc aacaccaagt gtcaaactcc aatgggggcg    900
ataaactcta gtatgccatt ccacaacata caccctctca ccatcgggga atgccccaaa    960
tatgtgaaat caaacagatt agtccttgcg acagggctca gaaatagccc tcaaagagag   1020
agaagaagaa aaaagagagg actatttgga gctatagcag gttttataga gggaggatgg   1080
cagggaatgg tagatggttg gtatgggtac caccatagca atgagcaggg gagtggatac   1140
gctgcagaca aagaatccac tcaaaaggca atagatggag tcaccaataa ggtcaactcg   1200
atcattgaca aaatgaacac tcagtttgag gccgttggaa gggaatttaa taacttagaa   1260
aggagaatag aaaatttaaa caagaagatg gaggacggat tcctagatgt ctggacttat   1320
aatgctgaac ttctggttct catggaaaat gagagaactc tagactttca tgactcaaat   1380
gtcaagaacc tttacgaaaa ggtccgacta caacttaggg ataatgcaaa ggagctgggt   1440
aacggttgtt tcgagttcta tcacaaatgt gataatgaat gtatggaaag tgtaaaaaac   1500
ggaacgtatg actacccgca gtattcagaa gaagcaagac taaacagaga ggaaataagt   1560
ggagtaaaat tggaatcaat aggaacttac caaatactgt caatttattc aacagtggtg   1620
agttccctag cactggcaat catggtagct ggtctatctt tatggatgtg ctccaatgga   1680
tcgttacaat gcagaatttg catttaa                                       1707
```

<210> SEQ ID NO 7
<211> LENGTH: 1707
<212> TYPE: DNA
<213> ORGANISM: Influenza A virus (A/chicken/Shanxi/2/2006)

<400> SEQUENCE: 7

```
atggagaaaa tagtgcttct tcttgcaata atcggtcttg ttaaaagtga tcagatttgc     60
gttggttacc atgcaaacaa ctcaacagag caggttgaca caataatgga aaagaacgtt    120
actgttacac atgctcaaga catactggag aagacacaca acgggaagct ctgcgaccta    180
gatggagtga agcctctcat tttgaaagat tgtagtgtag ctggatggct cctcggaaac    240
cctatgtgtg acgaatttat caatgtgtcg gaatggtctt acatagtgga gaaggccagt    300
ccagccaatg gcctctgtta cccaggggat ttcaatgact atgaagaact gaaacaccta    360
ttgagcagaa taaaccattt tgagaaaatt aagatcatcc ccaaaagttc ttggtccaat    420
catgaagcct catcaggggt gagctcagca tgttcctatc tggggaagcc ctcctttttc    480
agaaatgtgg tatggcttat caaaaagaat aatacatacc caccaataaa ggtgaactac    540
accaatacca accaagaaga tcttttggta ctgtggggga ttcaccatcc caacgatgag    600
acagagcaga taaagatcta tcaaaaccca accacctata tttccgttgg aacatcaaca    660
ctaaaccaga gattggtacc aaaaatagct actaaatccc aagtgaacgg gcaaagtgga    720
agaatggagt tcttctggac aattttaaag ccgaatgatg ctatcaattt cgatagtaat    780
ggaaatttca ttgctccaga atatgcatac aaaattgtca agaaagggga ctcagcgatt    840
atgaaaagtg aattggaata tggtaactgc aacaccaagt gtcaaactcc aatgggggcg    900
ataaattcta gtatgccatt ccacaacata caccctctca ccatcgggga atgccccaaa    960
tatgtgaaat caaacagatt agtcctcgcg actggactca gaaatgcccc tcaaagagag   1020
ggaagaagaa aaaagagagg actatttgga gccatagcag ggtttataga gggaggatgg   1080
```

```
cagggaatgg tagatggttg gtatgggtac caccatagca atgagcaggg gagtggatac   1140

tctgcagaca aagaatccac tcaaaaggca atagatggag tcaccaataa ggtcaactcg   1200

atcattgaca aaatgaacac tcagtttgag ggcgttgtta gggaaattaa taacttagaa   1260

aggagaatag agaatttaaa caaaaagatg gaagacggat tcctagatgt ctggacttat   1320

aacgctgaac ttctggttct catggaaaat gagagaactc tagactttca tgactcaaat   1380

gtcaagaacc tttacgacaa ggtccgactg cagcttaggg ataatgcaaa ggagctgggt   1440

aacggttgtt tcgaattcta tcacaaatgt gataatgaat gtatggaaag tgtaaaaaac   1500

ggaacgtatg actacccgca gtattcagaa gaagcaagac taaacagaga ggaaataagt   1560

ggagtaaaat tggaatcaat ggtaacttac caaatactgt caatttattc aacagtggcg   1620

agttccctag cattggcaat catggtggct ggtctatctt tatggatgtg ctccaatgga   1680

tcgttacaat gcagaatttg catttga                                       1707
```

<210> SEQ ID NO 8
<211> LENGTH: 1707
<212> TYPE: DNA
<213> ORGANISM: Influenza A virus (A/Chicken/Henan/12/2004)

<400> SEQUENCE: 8

```
atggagaaaa tagtgcttct tcttgcaata gtcagtcttg ttaaaagtga tcagatttgc     60

attggttacc atgcaaacaa ctcgacagag caggttgaca caataatgga aaagaacgtt    120

actgttacac atgcccaaga catactggaa aagacacaca acgggaagct ctgcgatcta    180

gatggagtga agcctctaat tttgagagat tgtagtgtag ctggatggct cctcggaaac    240

ccaatgtgtg acgaattcat caatgtgccg gaatggtctt acatagtgga gaaggccagt    300

ccagccaatg gcctctgtta cccaggggat ttcaacgact atgaagaact gaaacaccta    360

ttgagcagaa taaaccattt tgagaaaatt cagatcatcc ccaaaagttc ttggtccaat    420

catgaagcct catcaggggt gagctcagca tgcccatacc agggaaagtc ctcctttttc    480

agaaatgtgg tatggcttat caaaaagaac agtacatacc caacaataaa gaggagctac    540

aataatacca accaagaaga tcttttggta ctgtggggga ttcaccatcc taatgatgcg    600

gcagagcaga caaggctcta tcaaaaccca accacctata tttccgttgg aacatcaaca    660

ctaaaccaga gattggtacc aaaaatagct actagatcca aagtaaacgg gcaaagtgga    720

aggatggagt tcttctggac aattttaaaa ccgaatgatg caatcaactt cgagagtaat    780

ggaaatttca ttgctccaga atatgcatac aaaattgtca agaaagggga ctcagcaatt    840

atgaaaagtg aattggaata tggtaactgc aacaccaagt gtcaaactcc aatgggggca    900

ataaactcta gtatgccatt ccacaacata caccctctca ccatcgggga atgcccccaaa    960

tatgtgaaat caaacagatt agtccttgcg actgggctca gaaatagccc tcaaagagag   1020

agaagaagaa aaaagagagg actatttgga gctatagcag gttttataga gggaggatgg   1080

cagggaatgg tagatggttg gtatgggtac caccatagca atgagcaggg gagtggatac   1140

gctgcagaca aagaatccac tcaaaaggca atagatggag tcaccaataa ggtcaactcg   1200

atcattgaca aaatgaacac tcagtttgag gccgttggaa gggaatttaa taacttagaa   1260

aggagaatag agaatttaaa caagaagatg gaagacggat tcctagatgt ctggacttat   1320

aatgctgaac ttctggttct catggaaaat gagagaactc tagactttca tgactcaaat   1380

gtcaagaacc tttacgacaa ggtccgacta cagcttaggg ataatgcaaa ggagctgggt   1440

aacggttgtt tcgagttcta tcacaaatgt gataatgaat gtatggaaag tgtaagaaac   1500
```

```
ggaacgtatg actacccgca gtattcagaa gaagcaagac taaaaagaga ggaaataagt   1560

ggagtaaaat tggaatcaat aggaacttac caaatactgt caatttattc aacagtggcg   1620

agttccctag cactggcaat catggtagct ggtctatctt tatggatgtg ctccaatgga   1680

tcgttacaat gcagaatttg catttaa                                       1707
```

<210> SEQ ID NO 9
<211> LENGTH: 1695
<212> TYPE: DNA
<213> ORGANISM: Influenza A virus (A/duck/Guangxi/2775/2005)

<400> SEQUENCE: 9

```
atggagaaaa tagtgcttct tcttgcaata gtcagtcttg ttaaaagtga tcagatttgc     60

attggttacc atgcaaacaa ctcgacagag caggttgaca caataatgga aaagaacgtt    120

actgttacac atgcccaaga catactggaa aagacacaca atgggaagct ctgcgaccta    180

gatggggtga agcctctaat tttgagagat tgtagtgtag ctggatggct cctcgggaac    240

ccaatgtgtg acgaattcat caatgtaccg gaatggtctt acatagtgga gaaggccagt    300

ccagccaatg acctctgtta cccaggtgat ttcaacgatt atgaagaact gaaacaccta    360

ttgagcagaa taaaccattt tgagaaaatt cagatcatcc ccaaaagttc ttggcccaac    420

catgaagcct catcaggggt gagctcagca tgtccatacc tgggaaagcc ctcctttttc    480

agaaatgtgg tatggcttat caaaaagaac agtgcatacc caacaataaa gaggagctac    540

aataatacca accaagaaga tcttttggta ctgtggggga ttcaccatcc taatgatgag    600

acagagcaga caaagctcta tcaaaaccca accacttata tttccgttgg aacatcaaca    660

ctaaaccaga gattggtacc aaaaatagct accagatcca aagtaaacgg gcaaagtgga    720

aggatggagt tcttctggac aattttaaaa ccgaatgatg caatcaactt cgagagtaat    780

ggaaatttca ttgctccaga atatgcctac aaaattgtca agaaagggga ctcagcaatt    840

atgaaaagtg aattggaata tggtaactgc aacaccaaat gtcaaactcc aatgggggcg    900

ataaactcta gtatgccatt ccacaacata caccctctca ccatcgggga atgccccaaa    960

tatgtgaaat caaacagatt agtccttgcg actgggctca gaaatagccc tcaaagggag   1020

agaagaagaa aaaagagagg actatttgga gctatagcag gttttataga gggaggatgg   1080

cagggaatgg tagatggttg gtacggatac caccatagca atgagcaggg gagtggatac   1140

gctgcagaca aagaatccac tcaaaaggca atagatggag tcaccaataa ggtcaactcg   1200

atcattgaca aaatgaacac tcagtttgag gccgttggaa gggaatttaa taacttagaa   1260

aggagaatag agaatttaaa caagaagatg gaagacgggt tcctagatgt ctggacttat   1320

aatgctgaac ttctggttct catggaaaat gagcgaactc tagactttca tgactcaaat   1380

gtcaagaacc tttacgacaa ggtccgacta cagcttaggg ataatgcaaa agagctgggt   1440

aacggttgtt tcgagttcta tcacaaatgt gataatgaat gcatggaaag tgtaagaaac   1500

ggaacgtatg actacccgca ttattcagaa gaagcaaggc taaaaagaga ggaaataagt   1560

ggagtaaaat tggaatcaat aggaacttac caaatactgt caatttattc aacagtggca   1620

agttccctag cgctggcaat catggtagct ggtctatctt tatggatgtg ctccaatggt   1680

tcgttacaat gcaga                                                    1695
```

<210> SEQ ID NO 10
<211> LENGTH: 1707
<212> TYPE: DNA

<213> ORGANISM: Influenza A virus (A/Hong Kong/156/97)

<400> SEQUENCE: 10

```
atggaaagaa cagtgcttct tcttgcaaca gtcagtcttg ttaaaagtga tcagatttgc     60
attggttacc atgcaaacaa ctcgacagag caggttgaca caataatgga aaagaatgtt    120
actgttacac atgcccaaga catactggaa aggacacaca acgggaagct ctgcgatcta    180
aatggagtga agcctctcat tttgagggat tgtagtgtag ctggatggct cctcggaaac    240
cctatgtgtg acgaattcat caatgtgccg gaatggtctt acatagtgga gaaggccagt    300
ccagccaatg acctctgtta tccagggaat ttcaacgact atgaagaact gaaacaccta    360
ttgagcagaa taaaccattt tgagaaaatt cagatcatcc ccaaaagttc ttggtccaat    420
catgatgcct catcaggggt gagctcagca tgtccatacc ttgggaggtc ctcctttttc    480
agaaatgtgg tatggcttat caaaaagaac agtgcatacc caacaataaa gaggagctac    540
aataatacca accaagaaga tcttttggta ctgtgggggg ttcaccatcc taatgatgcg    600
gcagagcaga caaagctcta tcaaaatcca accacctaca tttccgttgg aacatcaaca    660
ctgaaccaga gattggttcc agaaatagct actagaccca aagtaaacgg gcaaagtgga    720
agaatggagt tcttctggac aattttaaag ccgaatgatg ccatcaattt cgagagtaat    780
ggaaatttca ttgctccaga atatgcatac aaaattgtca agaaagggga ctcaacaatt    840
atgaaaagtg aattggaata tggtaactgc aacaccaagt gtcaaactcc aatgggggcg    900
ataaactcta gtatgccatt ccacaacata cacccctca ccatcgggga atgccccaaa      960
tatgtgaaat caaacagatt agtccttgcg actggactca gaaataccc tcaaagagag    1020
agaagaagaa aaaagagagg actatttgga gctatagcag gttttataga gggaggatgg   1080
cagggaatgg tagatggttg gtatgggtac caccatagca atgagcaggg gagttgctac   1140
tctgcagaca aagaatccac tcaaaaggca atagatggag tcaccaataa ggtcaactcg   1200
atcattaaca aaatgaacac tcagtttgag gccgttggaa gggaatttaa taacttggaa   1260
aggaggatag agaatttaaa caagaagatg gaagacggat tcctagatgt ctggacttac   1320
aatgctgaac ttctggttct catggaaaat gagagaactc tcgactttca tgactcaaat   1380
gtcaagaacc tttacgacaa ggtccgacta cagcttaggg ataatgcaaa ggagctgggt   1440
aatggttgtt tcgaattcta tcacaaatgt gataatgaat gtatggaaag tgtaaaaaac   1500
ggaacgtatg actacccgca gtattcagaa gaagcaagac taaacagaga ggaaataagt   1560
ggagtaaaat tggaatcaat gggaacttac caaatactgt caatttattc aacagtggcg   1620
agttccctag cactggcaat catggtagct ggtctatctt tatggatgtg ctccaatgga   1680
tcgttacaat gcagaatttg catttaa                                       1707
```

<210> SEQ ID NO 11
<211> LENGTH: 1704
<212> TYPE: DNA
<213> ORGANISM: Influenza A virus (A/Anhui/1/2005)

<400> SEQUENCE: 11

```
atggagaaaa tagtgcttct tcttgcaata gtcagccttg ttaaaagtga tcagatttgc     60
attggttacc atgcaaacaa ctcgacagag caggttgaca caataatgga aaagaacgtt    120
actgttacac atgcccaaga catactggaa aagacacaca acgggaagct ctgcgatcta    180
gatggagtga agcctctgat tttaagagat tgtagtgtag ctggatggct cctcggaaac    240
ccaatgtgtg acgaattcat caatgtgccg gaatggtctt acatagtgga gaaggccaac    300
```

ccagccaatg acctctgtta cccagggaat ttcaacgact atgaagaact gaaacaccta 360
ttgagcagaa taaaccattt tgagaaaatt cagatcatcc ccaaaagttc ttggtccgat 420
catgaagcct catcaggggt gagctcagca tgtccatacc agggaacgcc ctccttttc 480
agaaatgtgg tatggcttat caaaaagaac aatacatacc caacaataaa gagaagctac 540
aataatacca accaggaaga tcttttgata ctgtggggga ttcatcattc taatgatgcg 600
gcagagcaga caaagctcta tcaaaaccca accacctata tttccgttgg gacatcaaca 660
ctaaaccaga gattggtacc aaaaatagct actagatcca aagtaaacgg gcaaagtgga 720
aggatggatt tcttctggac aattttaaaa ccgaatgatg caatcaactt cgagagtaat 780
ggaaatttca ttgctccaga atatgcatac aaaattgtca agaaagggga ctcagcaatt 840
gttaaaagtg aagtggaata tggtaactgc aacacaaagt gtcaaactcc aataggggcg 900
ataaactcta gtatgccatt ccacaacata caccctctca ccatcgggga atgccccaaa 960
tatgtgaaat caaacaaatt agtccttgcg actgggctca gaaatagtcc tctaagagaa 1020
agaagaagaa aaagaggact atttggagct atagcagggt ttatagaggg aggatggcag 1080
ggaatggtag atggttggta tggtaccac catagcaatg agcaggggag tgggtacgct 1140
gcagacaaag aatccactca aaaggcaata gatggagtca ccaataaggt caactcgatc 1200
attgacaaaa tgaacactca gtttgaggcc gttggaaggg aatttaataa cttagaaagg 1260
agaatagaga atttaaacaa gaaaatggaa gacggattcc tagatgtctg gacttataat 1320
gctgaacttc tggttctcat ggaaaatgag agaactctag acttccatga ttcaaatgtc 1380
aagaaccttt acgacaaggt ccgactacag cttagggata atgcaaagga gctgggtaac 1440
ggttgtttcg agttctatca caaatgtgat aatgaatgta tggaaagtgt aagaaacgga 1500
acgtatgact acccgcagta ttcagaagaa gcaagattaa aaagagagga aataagtgga 1560
gtaaaattgg aatcaatagg aacttaccaa atactgtcaa tttattcaac agttgcgagt 1620
tctctagcac tggcaatcat ggtggctggt ctatctttgt ggatgtgctc caatgggtcg 1680
ttacaatgca gaatttgcat ttaa 1704

<210> SEQ ID NO 12
<211> LENGTH: 1707
<212> TYPE: DNA
<213> ORGANISM: Influenza A virus (A/turkey/Turkey/1/05)

<400> SEQUENCE: 12
atggagaaaa tagtgcttct tcttgcaata gtcagccttg ttaaaagtga tcagatttgc 60
attggttacc atgcaaacaa ctcgacagag caggttgaca caataatgga aaagaacgtc 120
actgttacac acgcccaaga catactggaa aagacacaca acgggaaact ctgcgatcta 180
gatggagtga agcctctaat tttaagagat tgtagtgtag ctggatggct cctcgggaac 240
ccaatgtgtg acgaattcct caatgtgccg gaatggtctt acatagtgga gaagatcaat 300
ccagccaatg acctctgtta cccagggaat ttcaacgact atgaagaact gaaacaccta 360
ttgagcagaa taaaccattt tgagaaaatt cagatcatcc ccaaaagttc ttggtcagat 420
catgaagcct cagcaggggt gagctcagca tgtccatacc agggaaggtc ctcctttttt 480
agaaatgtgg tatggcttat caaaaaggac aatgcatacc caacaataaa gagaagttac 540
aataatacca accaagaaga tcttttggta ttgtggggga ttcaccatcc aaatgatgcg 600
gcagagcaga caaggctcta tcaaaaccca actacctata tttccgttgg gacatcaaca 660

```
ctaaaccaga gattggtacc aaaaatagcc actagatcta aggtaaacgg gcaaagtgga    720

aggatggagt tcttttggac aattttaaaa ccgaatgatg caataaactt tgagagtaat    780

ggaaatttca ttgctccaga aaatgcatac aaaattgtca agaaagggga ctcaacaatt    840

atgaaaagtg agttggaata tggtaactgc aacaccaagt gtcaaactcc aataggggcg    900

ataaactcta gtatgccatt ccacaacatc caccctctca ccatcgggga atgccccaaa    960

tatgtgaaat caagcagatt agtccttgct actgggctca gaaatagccc tcaaggagag   1020

agaagaagaa aaaagagagg actatttgga gctatagcag gttttataga gggaggatgg   1080

cagggaatgg tagatggttg gtatgggtac caccatagca acgagcaggg gagtgggtac   1140

gctgcagaca aagaatccac tcaaaaggca atagatggag tcaccaataa ggtcaactcg   1200

atcattgaca aaatgaacac tcagtttgag gctgttggaa gggaatttaa taacttagaa   1260

aggagaatag aaaatttaaa caagaagatg gaagacggat tcctagatgt ctggacttat   1320

aatgctgaac ttctggttct catggaaaat gagagaactc tagactttca tgactcaaat   1380

gtcaagaacc tttacgacaa ggtccgacta cagcttaggg ataatgcaaa ggagcttggt   1440

aacggttgtt tcgagttcta tcacagatgt gataatgaat gtatggaaag tgtaagaaac   1500

ggaacgtatg actacccgca gtattcagaa gaagcaagat taaaaagaga ggaaataagt   1560

ggagtaaaat tggaatcaat aggaacttac caaatactgt caatttattc aacagtggcg   1620

agctccctag cactggcaat catggtggct ggtctatctt tatggatgtg ctccaatgga   1680

tcgttacaat gcagaatttg catttaa                                       1707
```

<210> SEQ ID NO 13
<211> LENGTH: 8
<212> TYPE: PRT
<213> ORGANISM: Influenza A virus

<400> SEQUENCE: 13

```
Arg Glu Gly Arg Arg Arg Lys Arg
1               5
```

<210> SEQ ID NO 14
<211> LENGTH: 26
<212> TYPE: DNA
<213> ORGANISM: Artificial Sequence
<220> FEATURE:
<223> OTHER INFORMATION: Adjuvant oligonucleotide
<220> FEATURE:
<221> NAME/KEY: Variant
<222> LOCATION: 1, 3, 5, 7, 9, 11, 13, 15, 17, 19, 21, 23, 25
<223> OTHER INFORMATION: N = inosine

<400> SEQUENCE: 14

```
ncncncncnc ncncncncnc ncncnc                                          26
```

<210> SEQ ID NO 15
<211> LENGTH: 11
<212> TYPE: PRT
<213> ORGANISM: Artificial Sequence
<220> FEATURE:
<223> OTHER INFORMATION: Adjuvant polycationic peptide

<400> SEQUENCE: 15

```
Lys Leu Lys Leu Leu Leu Leu Leu Lys Leu Lys
1               5                   10
```

<210> SEQ ID NO 16
<211> LENGTH: 8

-continued

```
<212> TYPE: PRT
<213> ORGANISM: Influenza A virus

<400> SEQUENCE: 16

Gly Glu Arg Arg Arg Arg Lys Arg
1               5
```